US005912732A

United States Patent [19]
Sekine

[11] Patent Number: 5,912,732
[45] Date of Patent: Jun. 15, 1999

[54] SURFACE DETECTING APPARATUS

[75] Inventor: Akihiko Sekine, Tokyo, Japan

[73] Assignee: Kabushiki Kaisha Topcon, Tokyo, Japan

[21] Appl. No.: 08/885,031

[22] Filed: Jun. 30, 1997

[30] Foreign Application Priority Data

| Jul. 5, 1996 | [JP] | Japan | 8-194096 |
| Jul. 15, 1996 | [JP] | Japan | 8-202801 |
| Jul. 17, 1996 | [JP] | Japan | 8-205463 |

[51] Int. Cl.$^6$ ................................. G01N 21/88
[52] U.S. Cl. ..................... 356/237.5; 356/237.4
[58] Field of Search .................. 356/237, 237.4, 356/237.5

[56] References Cited

U.S. PATENT DOCUMENTS

| 4,376,583 | 3/1983 | Alford et al. | 356/237 |
| 5,105,092 | 4/1992 | Natsubori et al. | 356/237 |
| 5,321,495 | 6/1994 | Hagiwara et al. | 356/237 |
| 5,422,724 | 6/1995 | Kinney et al. | 356/237 |
| 5,581,348 | 12/1996 | Miura et al. | 356/237 |

Primary Examiner—Robert H. Kim
Assistant Examiner—Zandra V. Smith
Attorney, Agent, or Firm—Foley & Lardner

[57] ABSTRACT

A surface inspection apparatus comprises a light source, a scan optical system having a scanning means for scanning a wafer surface in a direction of crossing the wafer by luminous flux from the light source, a moving unit for moving the wafer relatively in a direction of a prescribed angle with respect to the scanning direction, a light receiving unit having a photoelectric converter for receiving scattered lights from the wafer surface, and a signal processing unit performing the the surface inspection based on signals from the light receiving unit. The scanning means is controlled to scan the luminous flux forward and rearward. The signal processing unit performs the surface inspection based on signals of the light receiving unit in a region excluding a transition area where scan is performed from the outside of the wafer to the wafer within a forward and rearward scan region by the scanning means.

13 Claims, 31 Drawing Sheets

F I G. 13
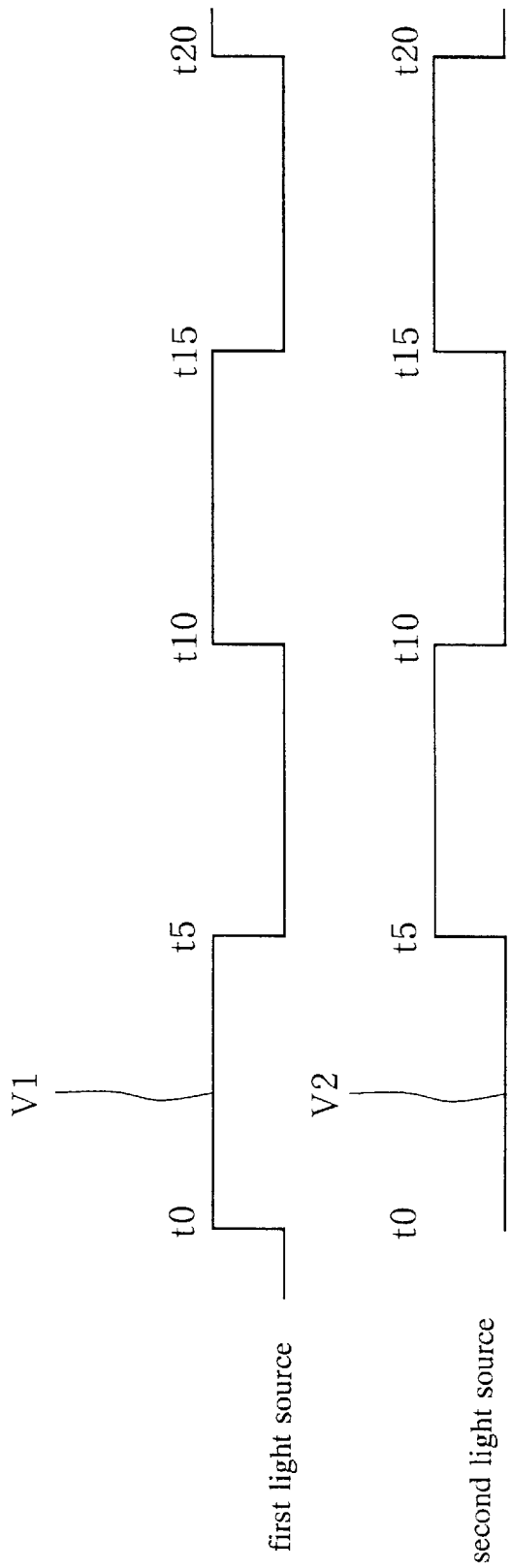

·········· scan line effective for inspection

──── right and left visual fields

SURFACE DETECTING APPARATUS

BACKGROUND OF THE INVENTION

The present invention relates to a surface inspection apparatus for inspecting a surface state of an object and more specifically to a surface inspection apparatus most suitable as a wafer surface inspection apparatus for inspecting a foreign substance, flaw or the like on a surface of a semiconductor wafer.

In general, a semiconductor integrated circuit is manufactured by forming a circuit on a semiconductor substrate (wafer) by photolithography process. In this case, a number of the same integrated circuits are formed on one sheet of wafer, and finally these circuits are separated into a number of single semiconductor integrated circuit chips. Then if a foreign substance exists on the wafer, a defect is produced in a circuit pattern formed on the part and the integrated circuit becomes unable to be used. As a result, the number of integrated circuits obtained from one sheet of substrate is decreased and the yield is lowered.

Such a foreign substance seems to adhere in CVD process where a metal film is formed on a wafer surface. That is, a foreign substance produced within a process apparatus adheres to a wafer leaving the apparatus, and becomes a defect in the lithography process afterward subjected to.

Therefore in the field of the semiconductor integrated circuit manufacturing, a wafer for inspection called a monitor wafer is used, and monitoring of generation of a foreign substance is performed. The wafer for inspection passes through the process apparatus in a similar manner to a material wafer, and the monitor wafer is inspected before or after the operation and if generation of a foreign substance is recognized, measures such as cleaning of the apparatus are taken.

As an inspection method, in general, laser beams are converged on a wafer surface and scattered lights from the converging point are received and a foreign substance or the like is detected from signals of the received lights.

FIG. 32 shows an example of a wafer surface inspection apparatus in the prior art.

A laser is used for a light source 121. Lights going out of the laser beam source 121 are converged on a surface of a wafer 101 by an optical system 125. The converged laser beams are scanned in one direction using a light deflector 123, a motor 126 or the like and a scan line SL is formed. At the same time, the wafer 101 is moved in direction orthogonal to the scan direction by a moving unit 110. As a result, the whole surface of the wafer 101 is scanned by the laser beams. The scattered lights from the converging point on the wafer 101 are received through a collector lens 127 of a light receiving unit 130 by a photoelectric converter 131. The photoelectric converter 131 receiving the scattered lights outputs signals of a pulse shape in response to the intensity of the scattered lights when the converging point crosses a foreign substance or the like. The size of the scattered object is decided depending on the amount of the signal output.

When the whole surface of the wafer is inspected by the laser beams, a scan range slightly wider than the wafer must be scanned. Because when the luminous flux is returned, there is a moment becoming the stationary state, and in general, in this point, a pulse signal can not be obtained and the inspection can not be performed.

However, when the scan range is set slightly wider than the wafer, following inconvenience is produced when lights strike an edge portion of the wafer.

That is, in the wafer surface inspection apparatus, a photoelectric converter of high sensitivity is used in order to detect weak scattered lights due to a foreign substance on the wafer. On the contrary, since the scattered lights produced at the edge of the wafer is significantly large in comparison with the scattered lights due to the foreign substance, the photoelectric converter does not act normally for a while after receiving the scattered lights produced at the edge of the wafer. Since the converging point is continued to be moved during this state, some range from the edge of the wafer can not be measured.

For example, when the beam is subjected to a raster scan and the measurement is performed at the scan state in one direction, a region incapable of being inspected is produced as shown in hatching in FIG. 33. The dimensions of this region become large as the scan speed of the beam becomes rapid. Consequently if the wafer becoming larger in diameter is to be inspected in a short time, the region incapable of being inspected becomes large and the exact inspection can not be performed.

SUMMARY OF THE INVENTION

An object of the present invention is to provide a surface inspection apparatus where a region incapable of being inspected due to scattered lights from an edge of an object of inspection such as a wafer is eliminated and the whole surface of the inspection object can be securely inspected.

In the first group (A) of the present invention, a surface inspection apparatus comprises a light source, a scan optical system provided with a scanning means for scanning a surface of an object in a direction of crossing the object by luminous flux from the light source, a moving unit for moving the object relatively in a direction of a prescribed angle with respect to the scanning direction, a light receiving unit provided with a photoelectric converter for receiving scattered lights from the surface of the object, and signals processing unit for performing the surface inspection based on signals from the light receiving unit.

The scanning means is controlled to scan the luminous flux in forward and rearward directions. The signal processing unit performs the surface inspection based on signals of the light receiving unit in a region excluding a transition area where scan is performed from the outside of the object to the object, within a region of scanning forward and rearward by the scanning means.

The surface inspection is performed regarding the whole region of the object. Consequently in the present invention, a substantially effective surface inspection is performed intermittently.

In a further preferable mode of the present invention, the signal processing unit performs the surface inspection based on signals of the light receiving unit at the latter half of the forward scan and signals of the light receiving unit at the latter half of the rearward scan by the scanning means. In this mode, the signal processing unit includes a signal storage unit for storing signals of the light receiving unit, and the signal storage unit stores the data at the latter half of the forward scan of the scanning means in the scan order and stores the data at the latter half of the rearward scan in the reverse order to the scan order, so that signals of the light receiving unit can be read out in a similar order to that in the case of scanning in such a manner as to cross the object.

Also the signal storage unit may store the data from the light receiving unit in the receiving order, and when the data are read out, the data at the latter half of the forward scan of the scanning means are outputted in the scan order and the data at the latter half of the rearward scan are outputted in the reverse order to the scan order, so that the data of the light receiving unit can be outputted in a similar order to that in the case of scanning in such a manner as to cross the object.

The light source unit may be controlled to be lit in a range excluding a transition area where scan is performed from the outside of the object to the object, within a region of scanning forward and rearward by the scanning means and to be put out in a range including the transition area other than the above-mentioned lighting region, and the signal processing unit may perform the surface inspection, based on signals of the light receiving unit in a region excluding the transition area where scan is performed from the outside of the object to the object, within the region of scanning forward and rearward by the scanning means.

In another mode of the present invention, the signal processing unit changes an arrangement of signals from the light receiving unit, and performs the surface inspection based on signals of the light receiving unit in a region excluding the transition area where scan is performed from the outside of the object to the object, within a region of scanning forward and rearward by the scanning means.

In the second group (B) of the present invention, a surface inspection apparatus comprises a light source, a scan optical system provided with scanning means for scanning luminous flux from the light source and converging lights to a surface to be inspected, a moving means for moving the surface of the object in a direction different from the scan direction of the scanning means, a light receiving unit provided with a photoelectric converter for receiving scattered lights from the converging point, and a signal processing unit for processing signals of the light receiving unit.

The scan optical system performs scan forward and rearward by two pieces of luminous flux, and the signal processing unit performs the signal processing based on signals in scan in a direction of the two pieces of scan luminous flux travelling from the object to the outside of the object. The whole region of the object is scanned at least one time by one of the two pieces of luminous flux. In one piece of luminous flux, a substantial surface inspection is performed intermittently.

In a further preferable mode of the present invention, the scanning means is provided with synchronizing means for control, so that at one of the two converging points moving forward and rearward, the scanning is made effective in the forward scan, and at the other of the two converging points, the scanning is made effective in the rearward scan.

Also the light source unit may include one light source, and the synchronizing means can change the luminous flux from the light source toward the two scan optical systems.

Further the light source unit may include at least two light sources of the same wavelength, and the synchronizing means may be provided with shutters in the optical path of the scan luminous flux from the two light sources.

In the third group (C) of the present invention, the surface detection apparatus comprises a light source, a scan optical system provided with a scanning means for scanning luminous flux from the light source in one direction and scanning a surface to be inspected, a moving means for moving the inspection object relatively in a direction different from the scan direction of the scanning means, a light receiving unit provided with a photoelectric converter for receiving scattered lights from the converging point, and a signal processing unit for processing signals from the light receiving unit.

The scan optical system in a wafer surface inspection apparatus scans linearly in parallel two pieces of luminous flux of the same wavelength, and the light receiving unit and the signal processing unit are constituted by two light receiving units for receiving scattered lights separately from the converging points produced by the two pieces of luminous flux.

The surface inspection apparatus is provided with a diaphragm unit for receiving only scattered lights of the prescribed region in each light receiving unit as above described, and a position of the diaphragm is varied in response to scan of the luminous flux. Since the diaphragm unit controlled in response to scan of the luminous flux is provided, the scattered lights can be received more securely and the inspection accuracy can be improved.

It is preferable that the position of the diaphragm unit be varied in synchronization with the scan luminous flux.

The prescribed range of each light receiving unit is a part of the object or the surface to be inspected, and it is preferable that the whole object or the whole surface to be inspected is set to be covered by the prescribed range of each light receiving unit.

BRIEF DESCRIPTION OF THE DRAWINGS

FIG. 13 is a wave form chart of a light source drive signal in the embodiment 1B;

DESCRIPTION OF THE EMBODIMENTS

Various embodiments of the present invention will be described separately in three groups A, B, C referring to the accompanying drawings as follows.

Group A (FIGS. 1–10)

Figure 1:
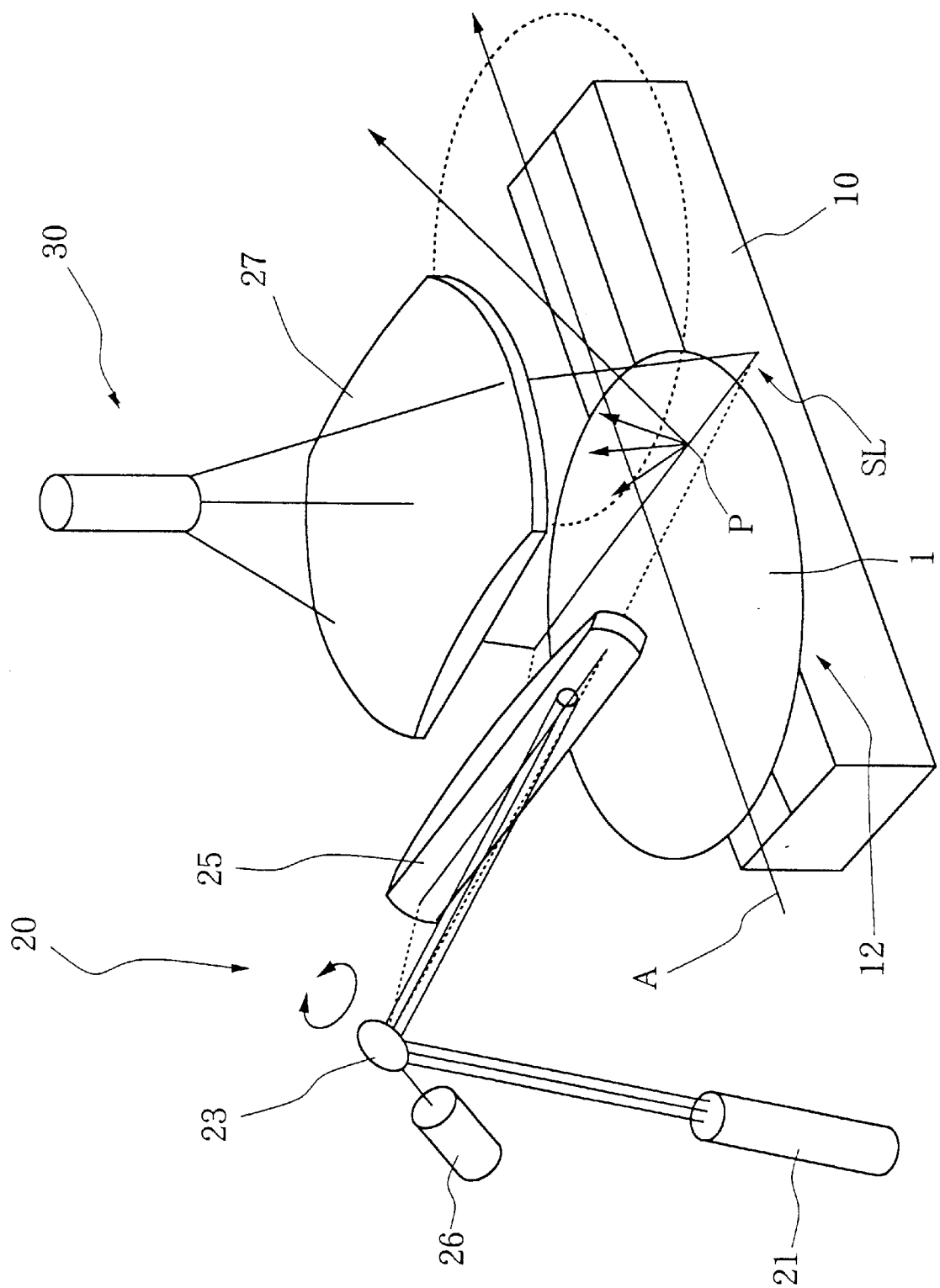
FIG. 1 is an optical arrangement diagram of an embodiment 1A of the invention.
Figure 2:
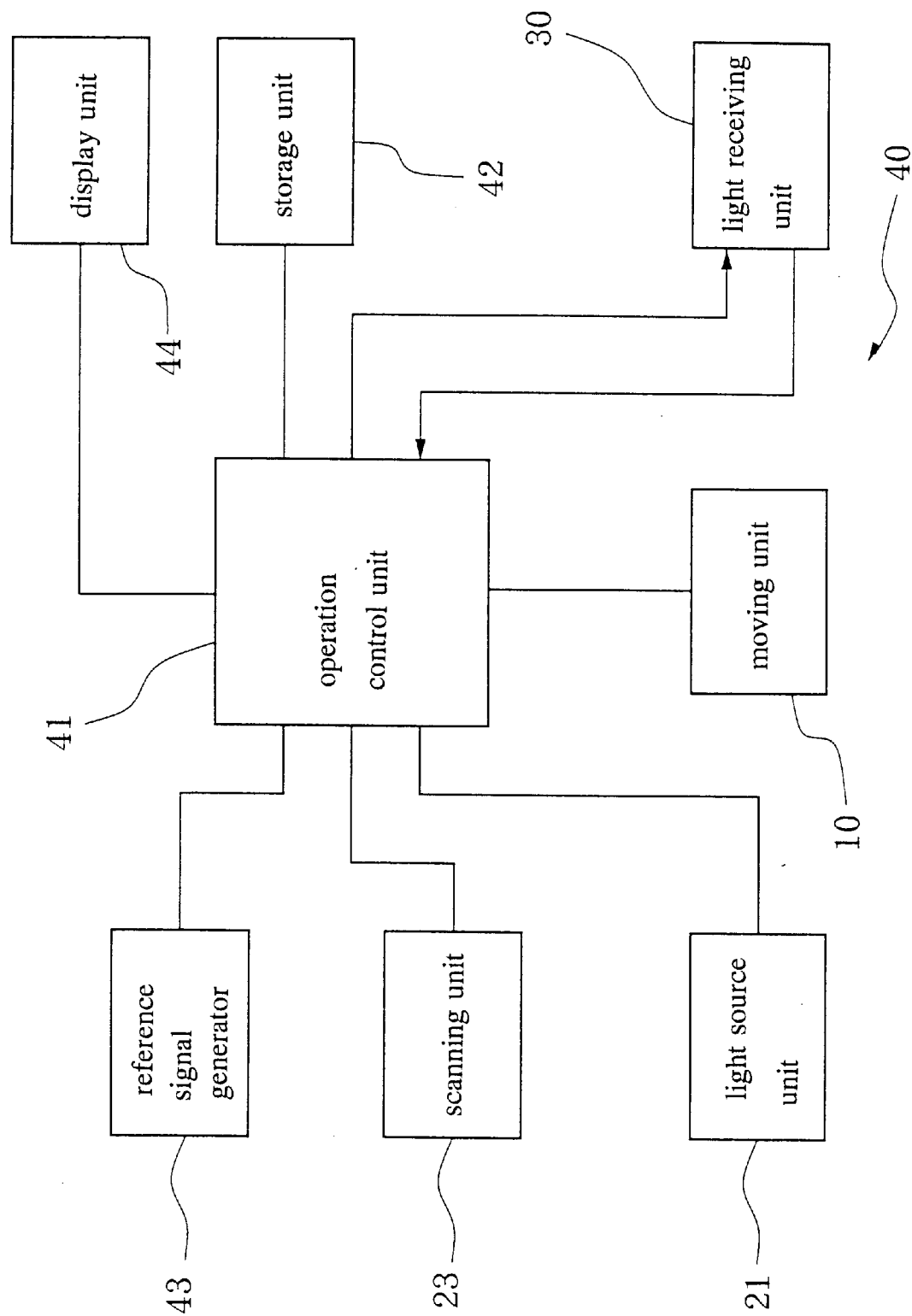
FIG. 2 is a block diagram of the embodiment 1A.

FIG. 1 is an optical arrangement diagram showing a surface inspection apparatus conceptually according to an embodiment 1A of the present invention, and FIG. 2 is a block diagram of the surface inspection apparatus.

The surface inspection apparatus according to the embodiment 1A comprises a moving unit 10, an optical system 20, a light receiving unit 30 and a signal processing unit 40.

The moving unit 10 is provided with a stage 12 movable forward and rearward at least in one direction. The stage 12 moves an object of inspection such as a wafer 1 (wafer is hereinafter described) in definite slow speed in the direction of arrow A shown in FIG. 1.

The optical system 20 is provided with a light source unit 21, a scanning mirror 23, a convergent lens 25 and a condenser lens 27.

The light source unit 21 is a laser beam source being strong in intensity, such as a semiconductor laser, and emits lights continuously while the whole wafer is scanned.

The scanning mirror 23 is rotated by a motor 26 corresponding to a scanning unit in response to signals from an operation control unit 41, and moves luminous flux from the light source unit 21 forward and rearward.

The convergent lens 25 converges lights from the light source onto a wafer being an object and forms a spot P. The spot P is scanned linearly on the wafer 1 by the rotation of the scanning mirror 23 and a scan line SL is formed.

The condenser lens 27 collects lights scattered by a foreign substance on the wafer onto a light receiving surface of an photoelectric converter. The condenser lens 27 is arranged in the direction and position where regular reflection lights by the scan lights generated from the light source and then regularly reflected on the wafer surface are not incident.

Next a scanning method by the optical system will be described.

Figure 4:
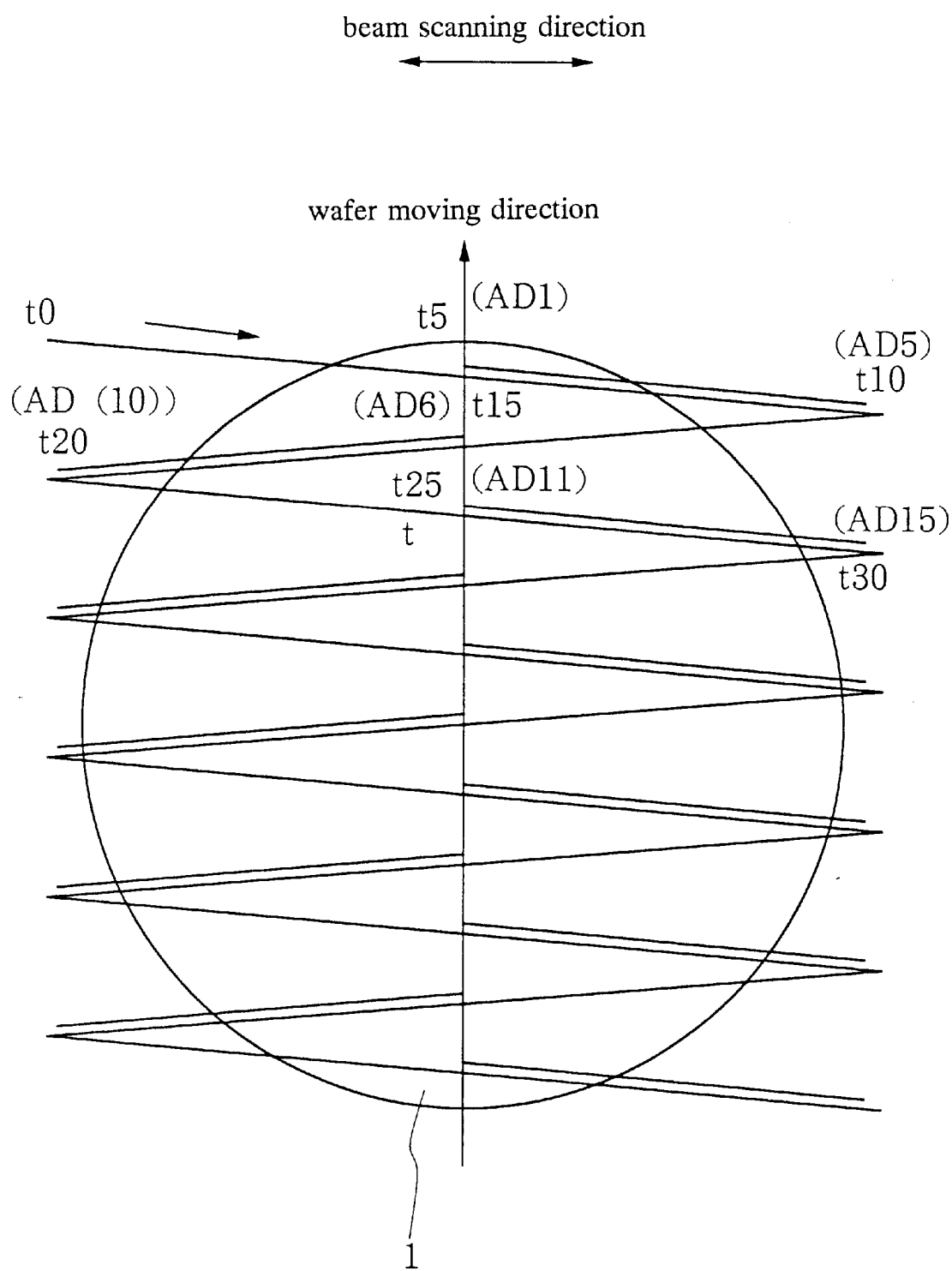
FIG. 4 is a diagram of data stored as data by a signal processing unit in the embodiment 1A shown on an object.

FIG. 4 shows relation between a scan line formed by beams and a part where lights received by a light receiving unit are stored as data. In order to make the explanation clear, the scan line is written coarsely. In the actual state, the beams densely scan the whole surface of the wafer.

In order to make the scan equivalent in the forward scan and the rearward scan, the scanning means performs the scan in the form of triangular waves and the light reception is made effective from the position where the beams attain to the center line of the wafer through a synchronizing means, and the data are acquired. The light reception is made ineffective from the transition area where scan is performed from the outside of the object to the prescribed region of the object, that is, the area where the beams attain from the outside of the wafer to the center line of the wafer in this embodiment. Consequently since influence of strong scattered lights produced by the beams striking the edge in the initial state at the first half of the scan is not exerted on the latter half, the inspection at the latter half is performed exactly.

On the other hand, also on the ending side at the latter half of the scan, although the beams may strike the edge and the strong scattered lights may be produced, since the rear side from this position corresponds to the outside of the wafer and need not be inspected, the inspection is not hindered on account of a similar reason. In other words, while the beams on the ending side of the scan produce the strong scattered lights and the photoelectric converter 31 described later does not act normally, no problem is offered since the spot P is moved in a part of the transition area as above described. Even if there is a substance immediately outside the wafer to be inspected so that luminous flux strikes the substance and scattered lights are produced, the inspection is not hindered and this serves also to decrease restrictions on producing the apparatus, accordingly.

The light receiving unit 30 is provided with a photoelectric converter 31. The photoelectric converter 31 receives lights scattered by a foreign substance irradiated by means of the scan lights, and outputs an electric signal in response to the scattered lights. As for the photoelectric converter, for example, a photomultiplier may be utilized.

Figure 3:
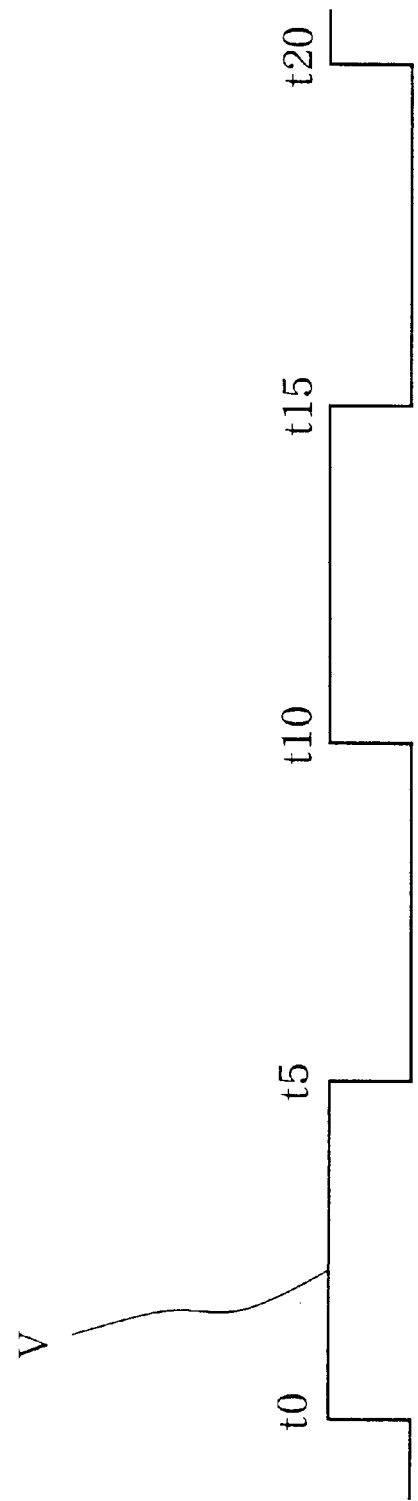
FIG. 3 is a wave form chart of a light source drive signal of the embodiment 1A.

The photoelectric converter 31 is constructed in such a manner as to output light receiving signals from the center portion of the wafer to the latter half during the forward scan and light receiving signals from the center portion of the wafer to the latter half during the rearward scan, based on a synchronous signal described later. A specific example of voltage applied to a photomultiplier of the photoelectric converter is shown in FIG. 3.

The signal processing unit 40 is provided with an operation control unit 41, a storage unit 42, a reference signal generator 43 and a display unit 44.

In this embodiment 1A, since only data at the latter half are fetched during the forward scan and the rearward scan as above described, signals do not appear in the order of scanning by one scan line. Consequently in order to treat the data as time series data showing from one end to other end of the wafer, the devising such as rearrangement of data is required.

That is, for the period from t0 to t5, data of scattered lights do not appear, and for the period from t5 to t10, data of scattered lights from the position L5 to the position L10 appear in sequence.

For the period from t10 to t15, data of scattered lights do not appear, and for the period from t15 to t20, data of scattered lights appear in sequence from the position L5 to the position L20.

Since an interval between the scan lines in the actual state is narrow, when the data order at the latter half of the rearward scan is reversed and the data for the period from t20 to t15 are connected with the data for the period from t15 to t10, the data can be treated in the state as if one scan line scanned the wafer and the signals of the scattered lights (whole scan data) could be obtained.

Here the processing by "system that assignment of the memory address is made the prescribed order during the data reading" will be described according to flow charts in FIG. 5 and FIG. 6.

Figure 5:
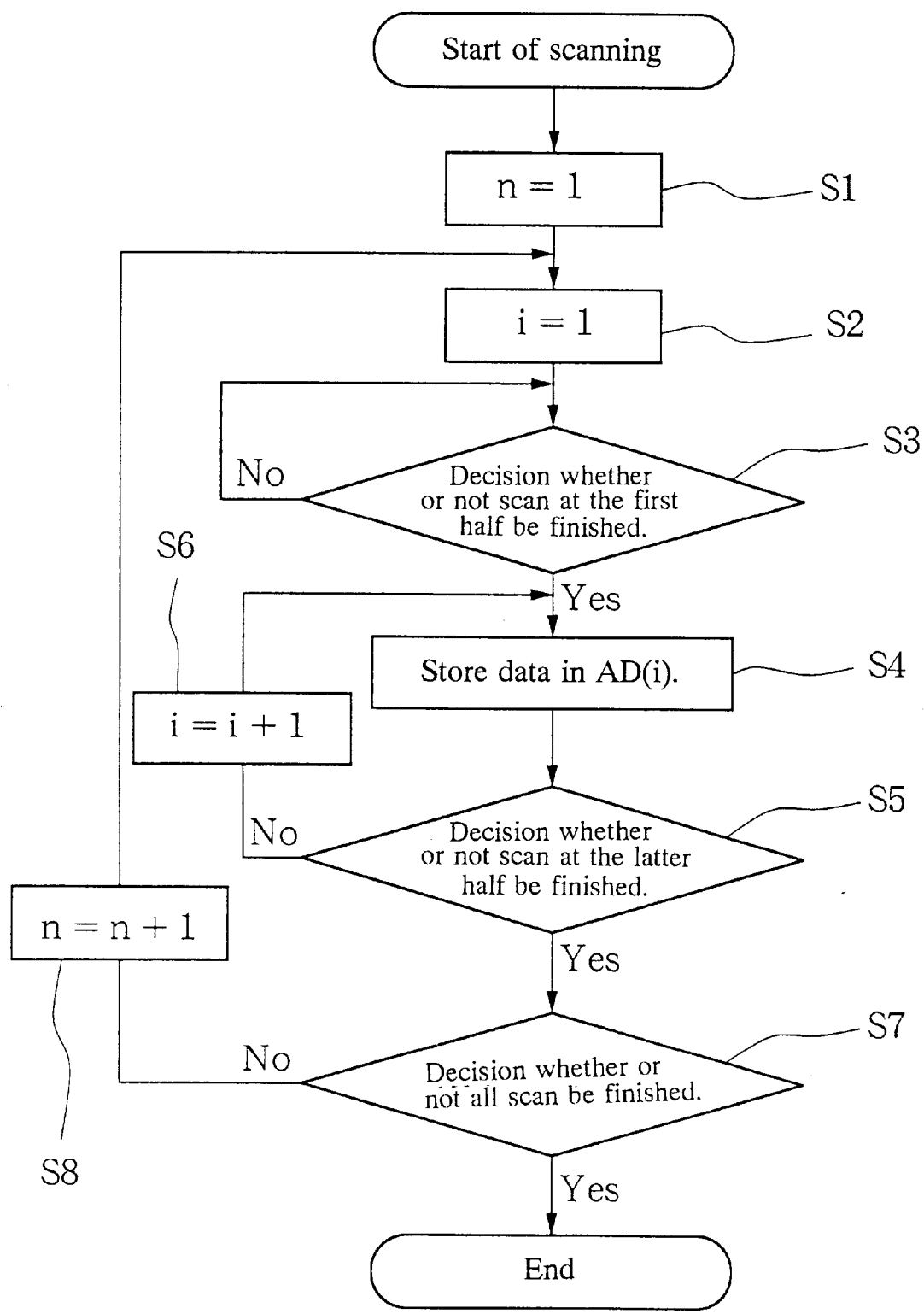
FIG. 5 is a flow chart of data storage in the embodiment 1A.

FIG. 5 is a flow chart for scan and storage.

S1: Scan times n be n=1.

S2: Number i be i=1.

S3; Decision whether scan at the first half be finished or not.

S4: Store data from a light receiving unit to address AD(i).

S5: Decision whether scan at the latter half be finished or not.

S6: Address position be i=i+1 and i is increased by 1. Return to S4, and store data during scan at the latter half to a memory.

S7: Decision whether all scan be finished or not.

S8: If not finished, n=n+1 and n is increased by 1, and return to S2.

Figure 6:
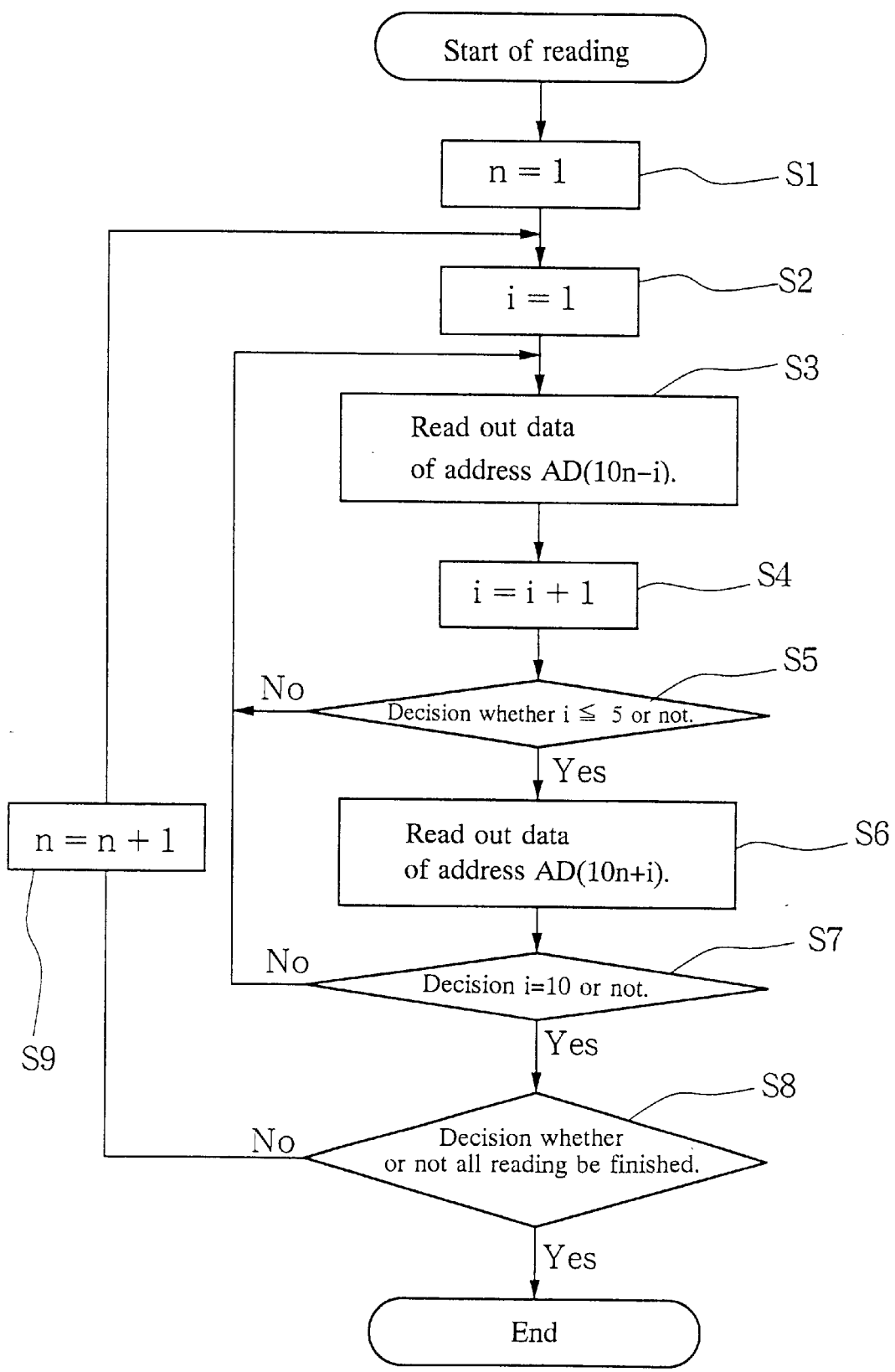
FIG. 6 is a flow chart of data reading in the embodiment 1A.

FIG. 6 is a flow chart for reading.

S1: Scan times n be n=1.

S2: Number i be i=1.

S3: Read out data of address AD (10n−i).

S4: Address position be i=i+1 and i is increased by 1.

S5: Decision whether scan at the first half or scan at the latter half depending on whether or not number i be 5 or less. If i be 5 or less and scan be at the first half, return to S3, and if i be more than 5 and scan be at the latter half, advance to S6.

S6: Read out data in address AD (10n+i).

S7: Decision whether number i be 10 or not. If number i be less than 10, return to S3, and if number i be 10, advance to S8.

S8: Decision whether reading be finished or not. If not finished, advance to S9.

S9: Scan times be n=n+1 and n is increased by 1, and return to S2.

In this system, the order of assignment of the memory address is devised during the data reading, and the whole scan data can be formed.

When the data are stored in the memory, signals from the photoelectric converter are stored in a state kept intact in a time series. In this case, the data are excluded from the storage object at the first half of the forward scan and at the first half of the rearward scan where the scanning is not made effective. Then the storage capacity of the memory can be utilized efficiently.

However, these data may be stored.

Showing a specific example, the scan is started and during the period at the first half of the forward scan (t0≦t<t5), the data are not stored, and during the period at the latter half of the forward scan (t5≦t<t10), the data are stored from the memory address AD1 to AD5 in sequence. During the period at the first half of the rearward scan (t10≦t<t15), the data are not stored, and during the period at the latter half of the rearward scan (t15≦t<t20), the data are stored from the memory address AD5 to AD10 in sequence.

When the data are read out, the data in the memory address from AD10 to AD6 corresponding to the data at the latter half of the rearward scan are read out in sequence from AD10 in the address decreasing direction to AD6, and the data in the memory address from AD1 to AD5 corresponding to the data at the latter half of the forward scan are read out in sequence from AD1 in the address increasing direction to AD5.

A similar processing is to be repeated, from now on.

Thereby the data stored to the memory address can be treated as signals of scattered lights (whole scan data) obtained in the state as if one scan line scans the wafer.

In the embodiment 1A as above described, luminous flux leaving the light source is scanned one-dimensionally and the wafer is moved in the substantially orthogonal direction to the scan direction so as to scan the whole surface of the wafer.

Figure 33:
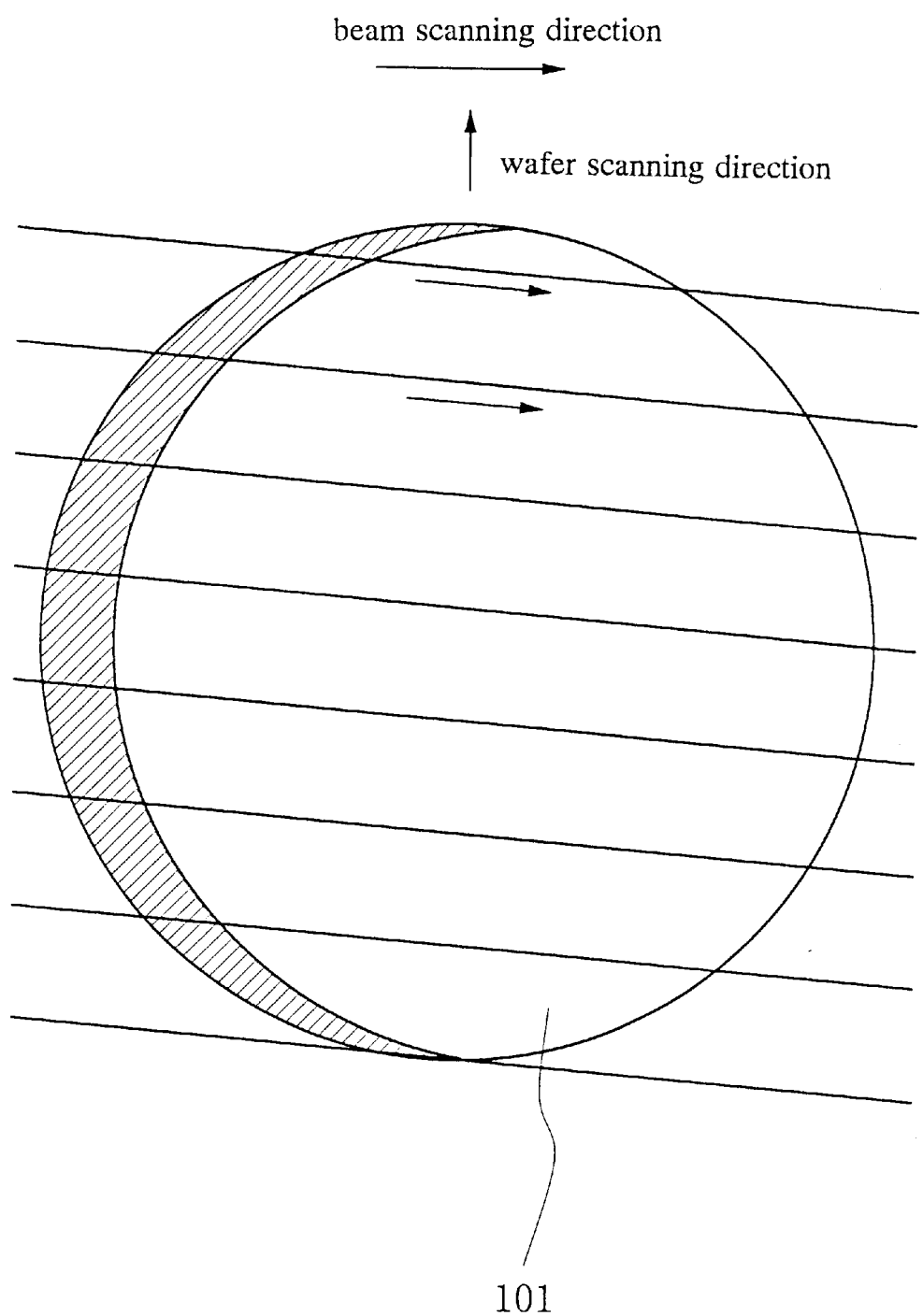
FIG. 33 is a diagram showing a region incapable of being inspected in the wafer surface inspection apparatus in the prior art shown in FIG. 32 when the wafer is subjected to raster scan.

If the light source unit is lit for the whole scan period, when the luminous flux strikes the edge of the wafer and the scattered light enters the light receiving unit, the light receiving unit is saturated and then for a while an area incapable of being measured (hatched portion in FIG. 33) is formed. Consequently in the present invention, data are taken after lapse of the time incapable of being inspected due to the scattered lights at the edge of the wafer, and this is performed also in the scan in the reverse direction so that the data can be taken on substantially the whole surface excluding a small part above and below the wafer.

In the embodiment 1A as above described, in order to minimize the region where data are taken doubly, the inspection is started from the time when the luminous flux attains to the center line of the wafer.

Next, another embodiment 2A of the present invention will be described.

The embodiment 2A is a modification of the signal processing unit in the embodiment 1A.

That is, in order to rearrange data to treat the data as time series data showing from one end to other end of the wafer, as a system separate from the embodiment 1A, "system that the assignment of the memory address is made the prescribed order during the data storage" may be adopted.

Figure 7:
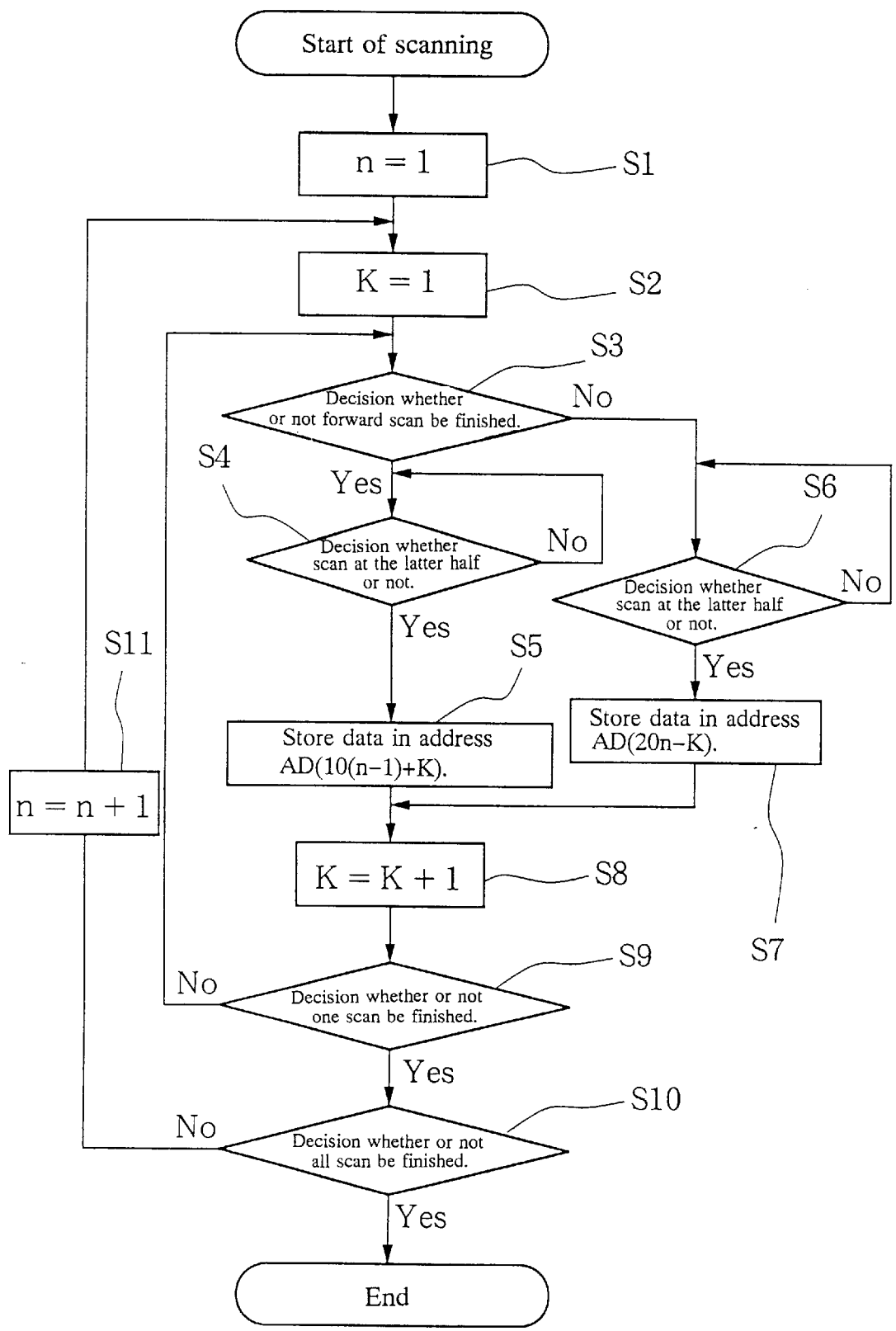
FIG. 7 is a flow chart of data storage in another embodiment 2A of the invention.

"System that assignment of the memory address is made the prescribed order during the data storage" will be described referring to a flow chart in FIG. 7. This is a system in which the whole scan data can be formed by devising the order of assignment of the memory address when the data are stored in the memory.

S1: Scan times n be n=1.

S2: Number k (corresponding to a scan position or a scan time ti) be k=1.

S3: Decision whether forward scan or not. If forward scan, advance to S4, and if rearward scan, advance to S6.

S4: Decision whether scan at the latter half or not. If not scan at the latter half, decision is repeated. If scan at the latter half, advance to S5.

S5: Store data in address AD (10) (n−1)+k), and advance to S8.

S6: Decision whether the latter half of rearward scan or not.

S7: Store data in address AD (20n−k), and advance to S8.

S8: k=k+1 and k is increased by 1.

S9: Decision whether one scan be finished or not. If not finished, return to S3.

S10: Decision whether all scan be finished or not.

S11: If not finished, n=n+1 and n is increased by 1, and return to S2.

Figure 8:
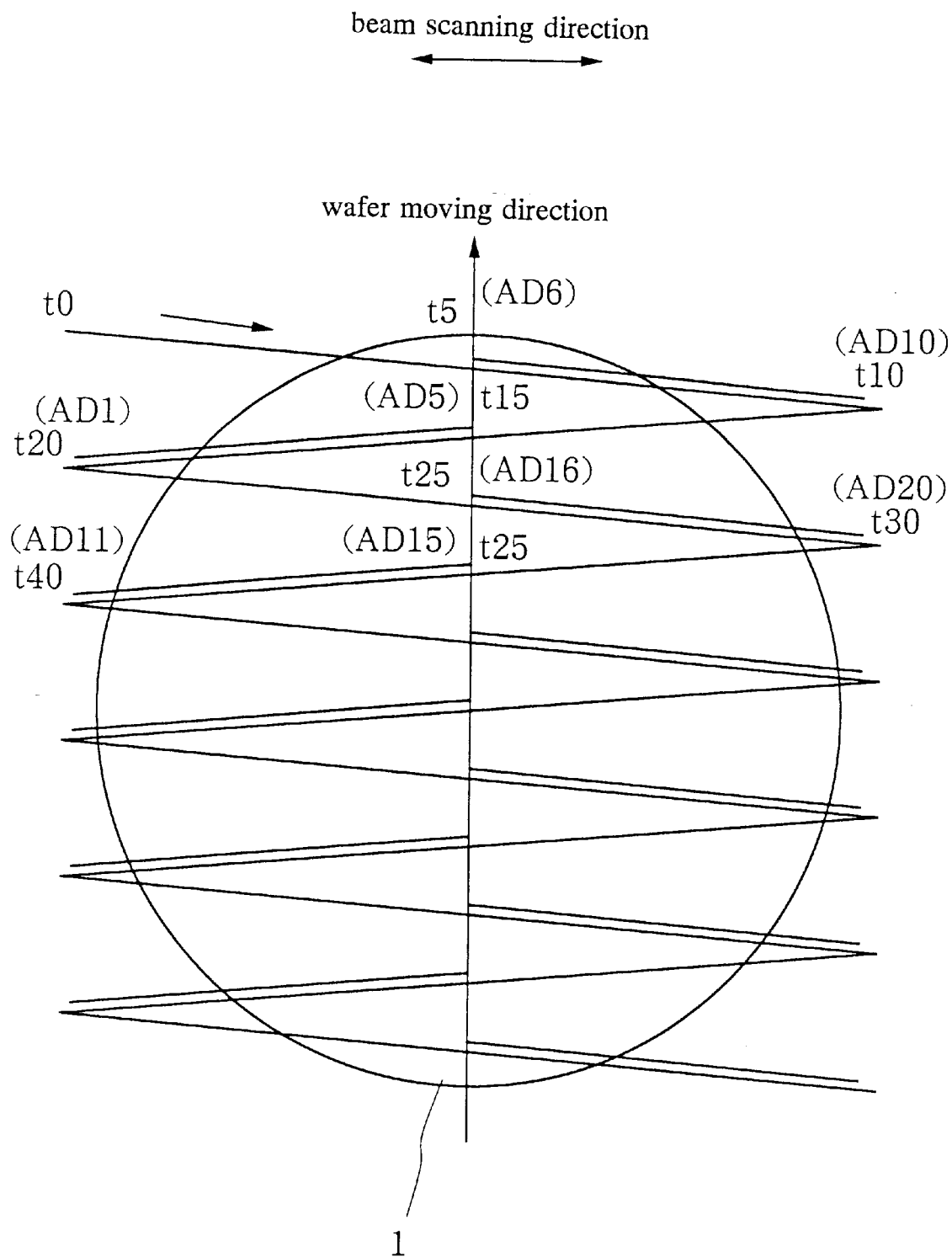
FIG. 8 is a diagram of data stored as data by a signal processing unit in the embodiment 2A shown on an object.

FIG. 8 shows data stored in the memory and the address number on the object.

Showing a specific example, the scan is started and during the period at the first half of the forward scan (t0≦t<t5), the data are not stored, and during the period at the latter half of the forward scan (t5≦t<t10), the data are stored from the memory address AD6 to AD10 in sequence.

Next, during the period at the first half of the rearward scan (t10≦t<t15), the data are not stored, and during the period at the latter half of the rearward scan (t15≦t<t20), the data are stored from the memory address AD5 to AD1 in sequence.

In this case, the data for the period at the latter half of the rearward scan are stored in sequence from the memory address AD5 to AD1 in the address decreasing direction.

A similar processing is to be repeated, from now on.

Thereby the data stored in the memory address from AD1 to AD10 can be treated as signals of scattered lights (whole scan data) obtained in the state as if one scan line scans the wafer.

In this case, when the memory address is read out in sequence, the whole scan data can be obtained.

Next, an embodiment 3A will be described.

In the embodiment 3A, only in a region other than a transition area where scan is performed from the outside of the object to the object, that is, a region of detecting the data, a light source unit is lit, while in the transition area, the light source unit is not lit. Also a signal processing unit performs a surface inspection, based on signals of a light receiving unit in the region excluding the transition area where the scan is performed from the outside of the object to the object, within the region of the forward and rearward scan by the scanning means.

To put it concretely, a lighting control is performed by sending signals in similar timing to that of the signal shown in FIG. 3 from an operation control circuit so that the light source unit is put out in the range from t1 to t5 including the transition area and is lit in the range other than this.

Further following modification may be used.

While the light source unit is lit continuously, luminous flux is interrupted mechanically by a shutter or the like in similar timing to that of the signal shown in FIG. 3, whereby similar scan becomes possible.

In the embodiment 1A, although the whole surface scan data are formed by connecting the data at the latter half of the forward scan with the data at the latter half of the rearward scan, the regions overlapping each other may be provided and the data may be received.

In this case, the connection of the data can be secured by comparing the data in the overlapping regions.

Figure 9:
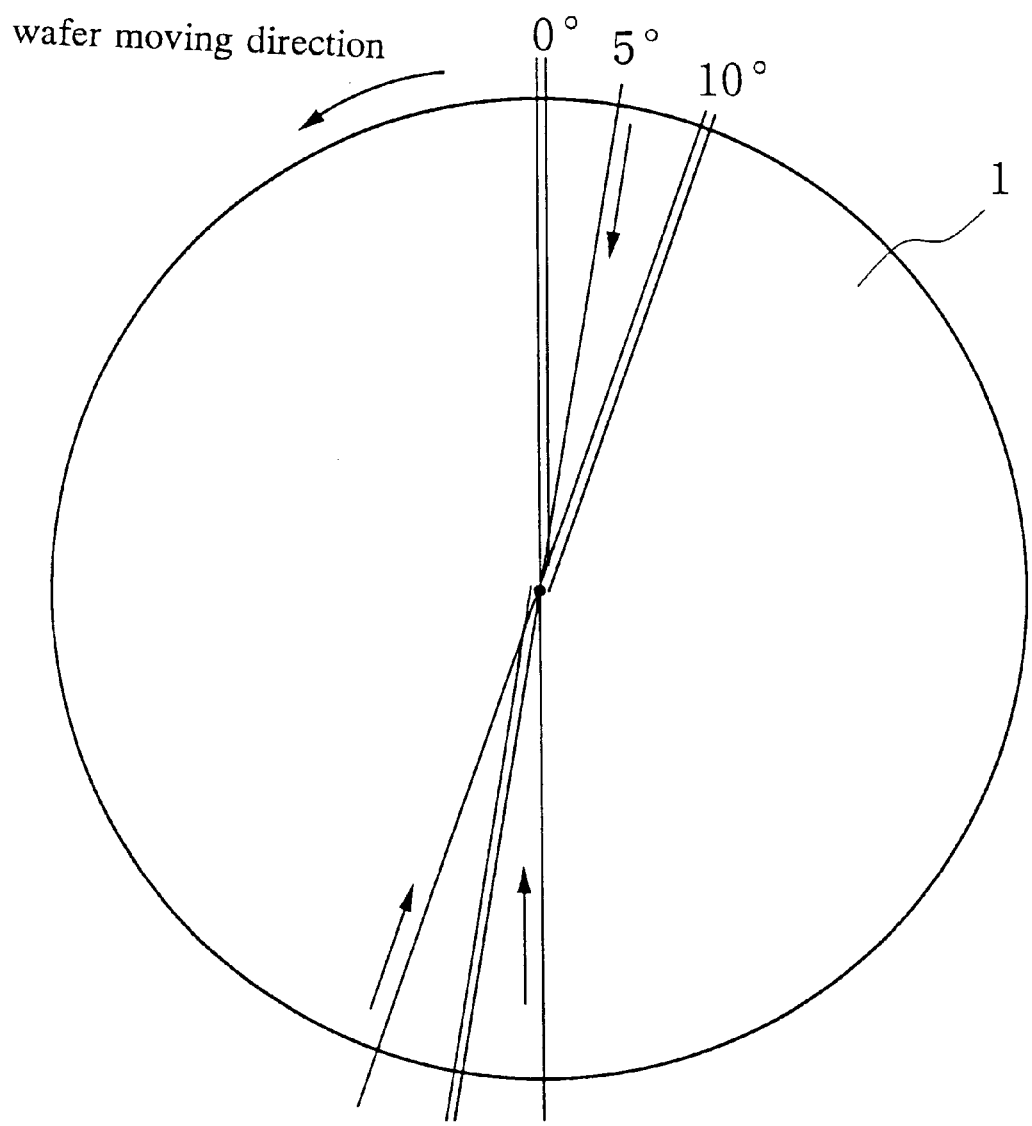
FIG. 9 is a diagram showing a modification of a system of rotating and moving a moving unit in the embodiment 2A.
Figure 10:
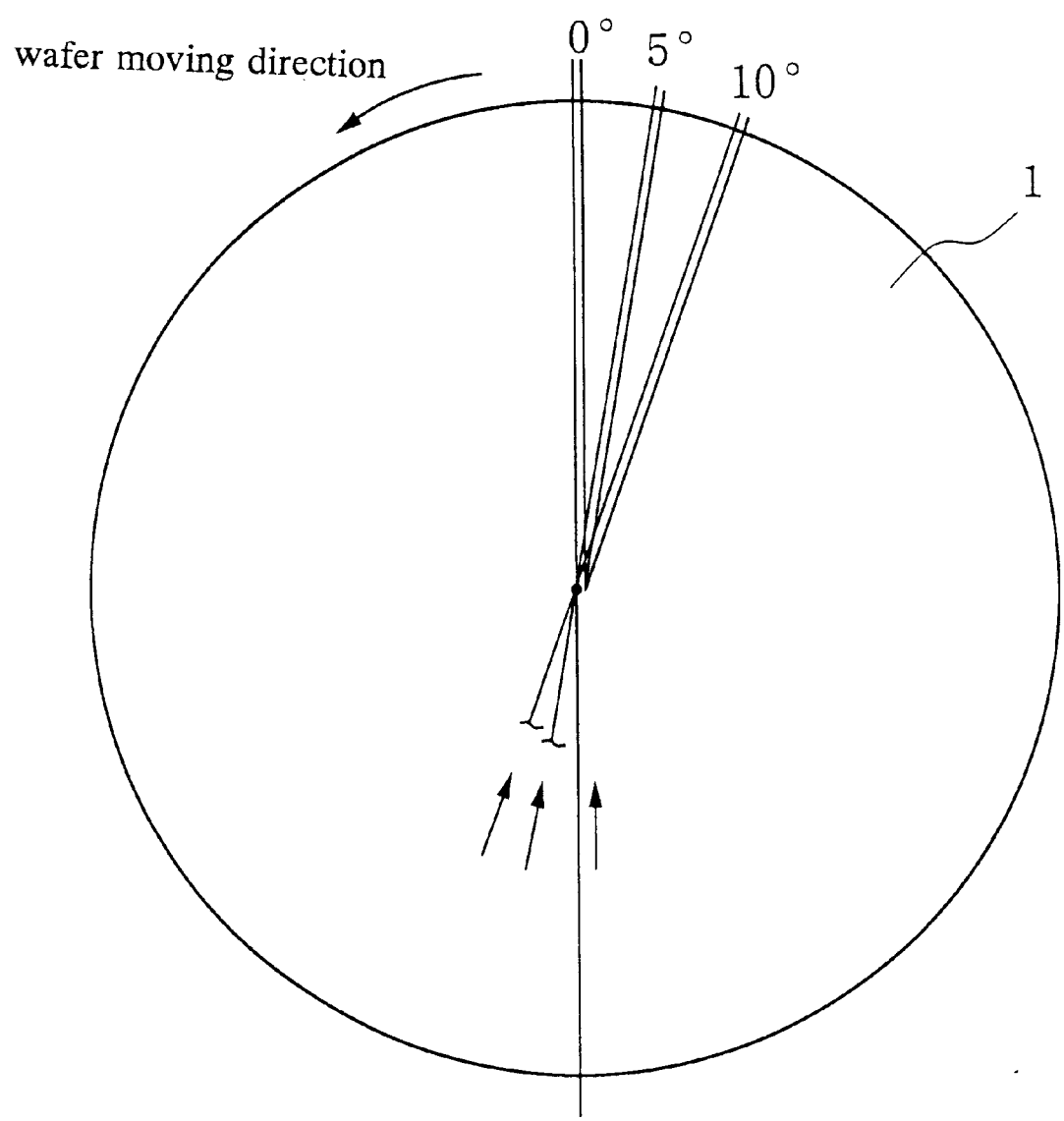
FIG. 10 is a diagram showing an example of another system of rotating and moving a moving unit in the embodiment 2A.

Further as shown in FIG. 9 and FIG. 10, a moving unit 10 can be constituted so that a stage 12 is rotatably moved. In the embodiment as above described, although the center line along the moving direction of the wafer is made the boundary between the first half and the latter half, when the wafer is rotatably moved, the center point of the wafer is made the boundary between the first half and the latter half (data acquisition).

In the rotary system of FIG. 9, signals obtained in the scan at the latter half are stored both in the forward scan and the rearward scan, and the rearranging processing is performed in a similar manner to the above mentioned system whereby the inspection result can be treated as the continuous diameter address.

In the rotary system of FIG. 10, signals obtained in the scan of the double line region of the forward scan are stored in time series in the order of smaller address, and during the reading, the signals are called in sequence in the order of smaller address whereby the data scanned from the center in the peripheral direction can be obtained. The system in FIG. 10 is a radius address system, and the performing of the forward and rearward scan slightly exceeding the length of the radius is sufficient.

According to the surface inspection apparatus as above described, a part near the edge of the wafer can be securely inspected although it was not able to be inspected conventionally, and the possibility of overlooking the generation of the foreign substance can be reduced.

Group B (FIGS. 11–21)

Figure 11:
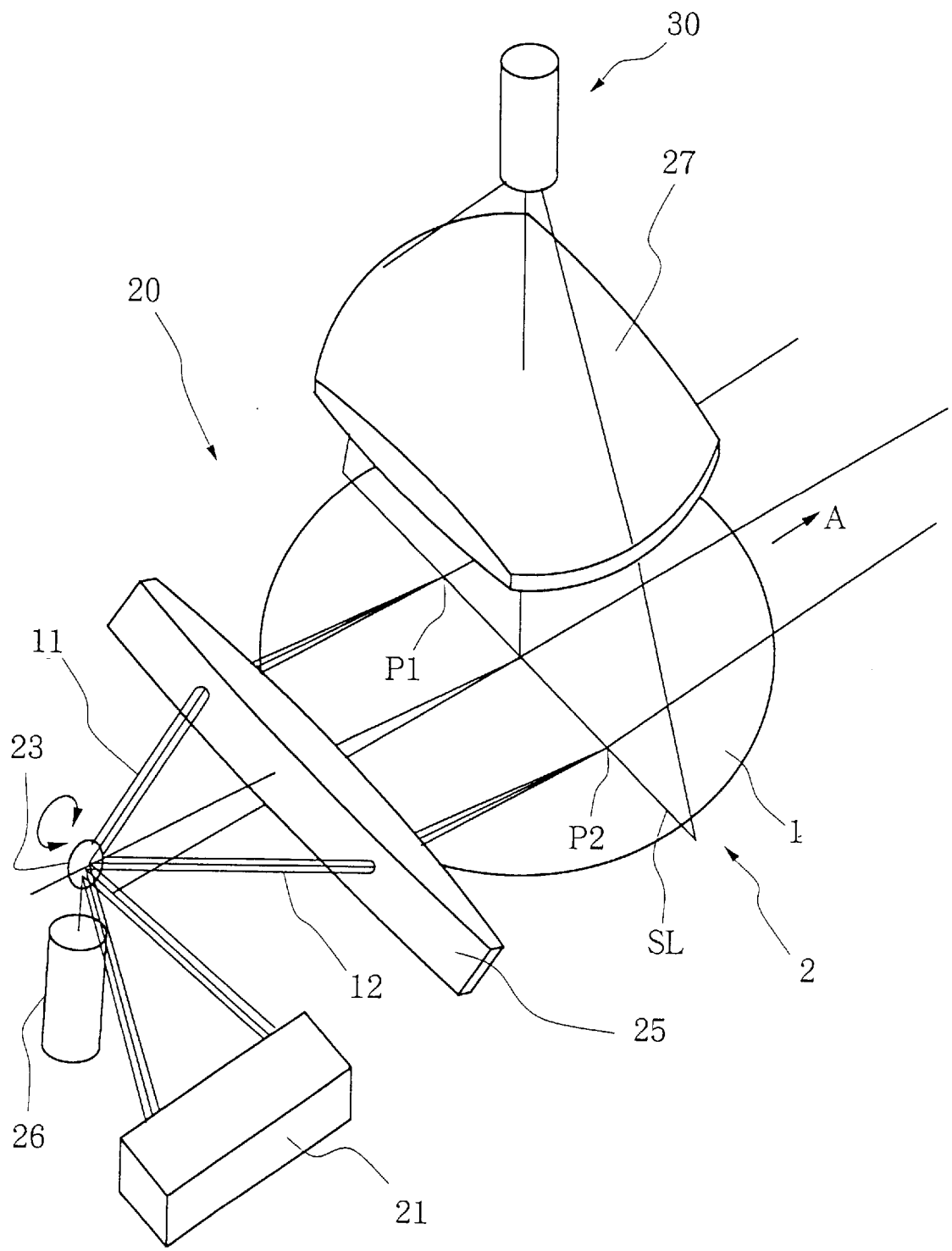
FIG. 11 is an optical arrangement diagram of still another embodiment 1B of the invention.
Figure 12:
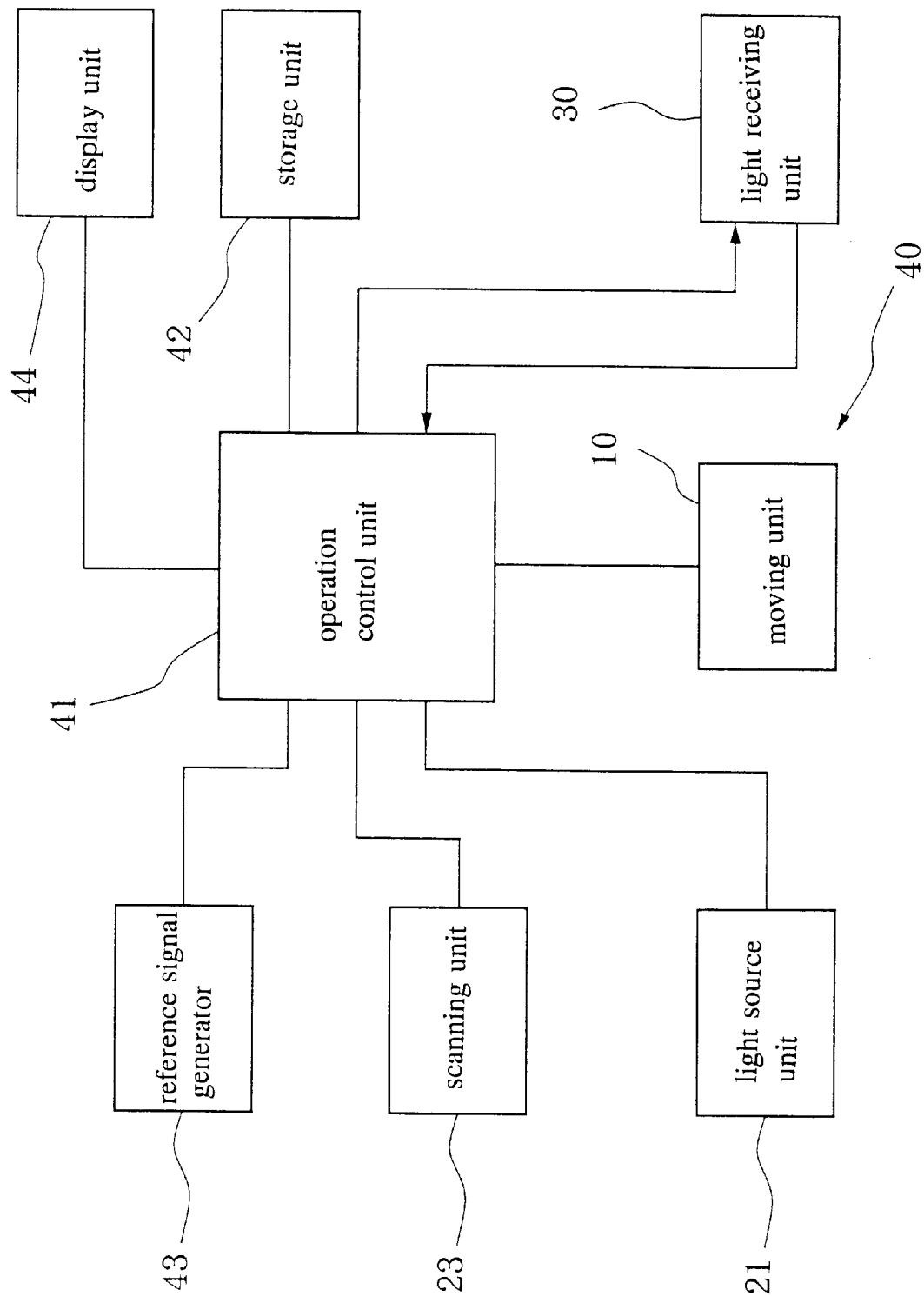
FIG. 12 is a block diagram of the embodiment 1B.

FIG. 11 is an optical arrangement diagram showing a surface inspection apparatus conceptually according to still another embodiment 1B of the present invention, and FIG. 12 is a block diagram of the surface inspection apparatus.

The surface inspection apparatus according to the embodiment 1B comprises a moving unit 10, an optical system 20, a light receiving unit 30 and a signal processing unit 40.

The moving unit 10 is provided with a stage 2 movable forward and rearward at least in one direction. The stage 2 moves an object such as a wafer 1 in definite slow speed in the direction of arrow A shown in FIG. 11.

In FIG. 11, the stage 2 is below the wafer 1 and is hidden.

The optical system 20 is provided with a light source unit 21, a scanning mirror 23, a convergent lens 25 and a condenser lens 27.

The light source unit 21 is provided with first and second laser beam sources being strong in intensity, such as a semiconductor laser, and is arranged such that luminous flux 11 and luminous flux 12 of the first and second laser beam sources divide into substantially two ranges the surface of the wafer 1 being an inspection object and are caused to be incident in the direction capable of scanning respectively.

Based on signals V1, V2 shown in FIG. 13, the first light source and the second light source are lit alternately, and at the forward scan (t0–t5), the luminous flux 11 emitted from the first light source scans, and at the rearward scan (t5–t10), the luminous flux 12 emitted from the second light source scans.

Figure 19:
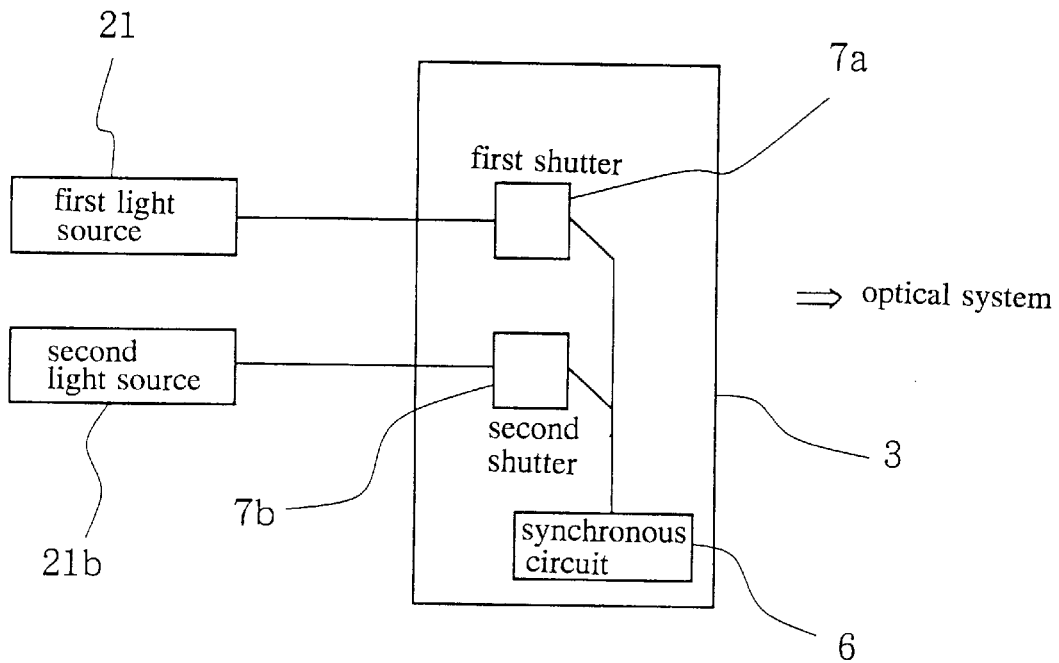
FIG. 19 is a diagram showing an example of a luminous flux changing means in the embodiment 2B.

As shown in FIG. 19, first and second shutters 7a, 7b may be provided and may be opened and closed in synchronization by a synchronous circuit 6 whereby beams from the first and second light sources 21a, 21b can be obtained alternately.

The scanning mirror 23 is rotated by a light deflector 26 corresponding to a scanning unit in response to signals from an operation control unit 41, and the luminous flux 11 and the luminous flux 12 emitted from the light source unit 21 are moved forward and rearward.

The convergent lens 25 converges the first luminous flux 11 and the second luminous flux 12 emitted from the light source 21 onto the wafer 1 being the object and forms spots P1, P2. The spots P1, P2 are scanned linearly on the wafer 1 by the rotation of the scanning mirror 23 and a scan line SL is formed.

The condenser lens 27 collects lights scattered by a foreign substance on the wafer 1 onto the light receiving surface of the photoelectric converter. The condenser lens 27 is arranged in the direction and the position where regular reflection light by the scan light produced from the light source and reflected in regular reflection on the wafer surface is not incident.

Next a scanning method according to the optical system will be described.

In the embodiment of the group B, the scan from the right to the left is defined as the forward scan and the scan from the left to the right is defined as the rearward scan. Also in FIG. 14, the left side is made the first luminous flux side and the right side is made the second luminous flux side.

In the embodiment of the group B, in the forward scan, the first light source is lit and the first luminous flux scans, while in the rearward scan, the second light source is lit and the second luminous flux scans.

Figure 14:
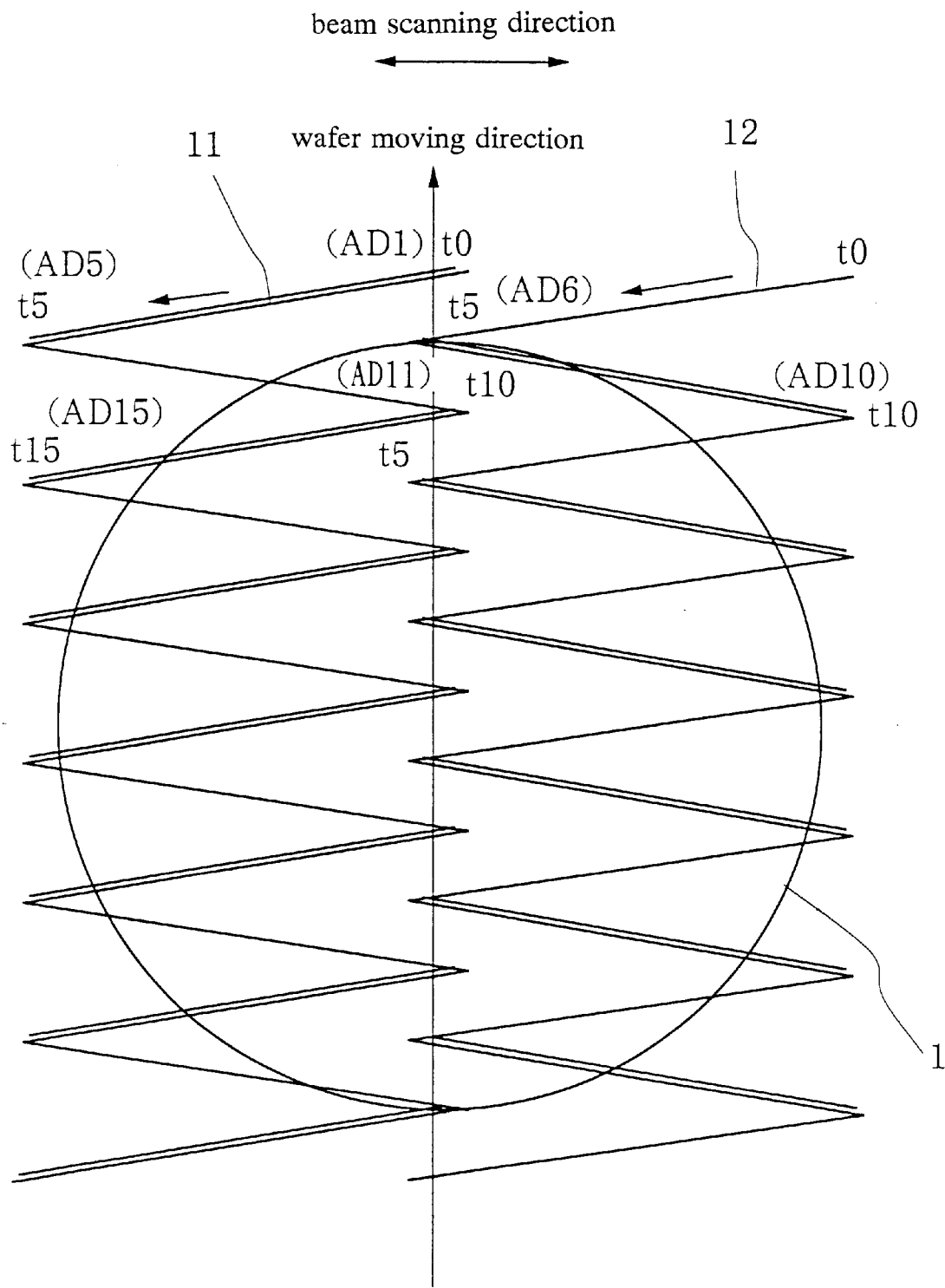
FIG. 14 is a diagram of data stored as data by a signal processing unit in the embodiment 1B shown on an object.

In FIG. 14, in order to make the explanation clear, the scan line is written coarsely. However, in the actual state, the beams scan the whole surface of the wafer 1 densely.

Describing the first luminous flux side taken as an example, the beams strike the edge and the strong scattered lights are produced in the vicinity of the end of the forward scan or on the midway of the forward scan, however, since the rear side from this position corresponds to the outside of the wafer and need not be inspected, the inspection is not hindered. That is, while the strong scattered lights are produced in the vicinity of the end of the forward scan of the beam or on the midway of the forward scan and therefore the photoelectric converter 31 described later does not act normally, no problem is offered since the spot P1 is moved on the outside of the wafer and at a part of the rearward path (transition area). Also even if there is a substance immediately outside the wafer to be inspected so that the luminous flux strikes the substance and the scattered lights are produced, the inspection is not hindered on account of a similar reason, and this serves to decrease restrictions on making the apparatus.

The light receiving unit 30 is provided with a photoelectric converter 31. The photoelectric converter 31 receives lights scattered by a foreign substance irradiated by means of the scan lights and outputs an electric signal in response to the scattered lights. As the photoelectric converter, for example, a photomultiplier may be utilized. In the forward scan, the scattered lights by the first luminous flux are received, and in the rearward scan, the scattered lights by the second luminous flux are received.

The signal processing unit 40 is provided with an operation control unit 41, a storage unit 42, a reference signal generator 43 and a display unit 44.

Since only the data of the forward scan are taken on the first luminous flux side and only the data of the rearward scan are taken on the second luminous flux side as above described, signals do not appear in the order of scanning by one scan line. Consequently in order to treat the data as time series data showing from one end to other end of the wafer, the devising such as rearrangement of the data is required.

That is, for the period from t0 to t5, data of scattered lights do not appear, and for the period from t5 to t10, data of scattered lights from the position L5 to the position L10 appear in sequence.

For the period from t10 to t15, data of scattered lights do not appear, and for the period from t15 to t20, data of scattered lights from the position L15 to the position L20 appear in sequence.

Since an interval between the scan lines in the actual state is narrow, the data order at the latter half of the rearward scan is reversed, and the data for the period from t20 to t15 can be connected with the data for the period from t5 to t10. Consequently the data can be treated in the state as if one scan line scanned the wafer and the signals of the scattered lights (whole scan data) could be obtained.

Figure 15:
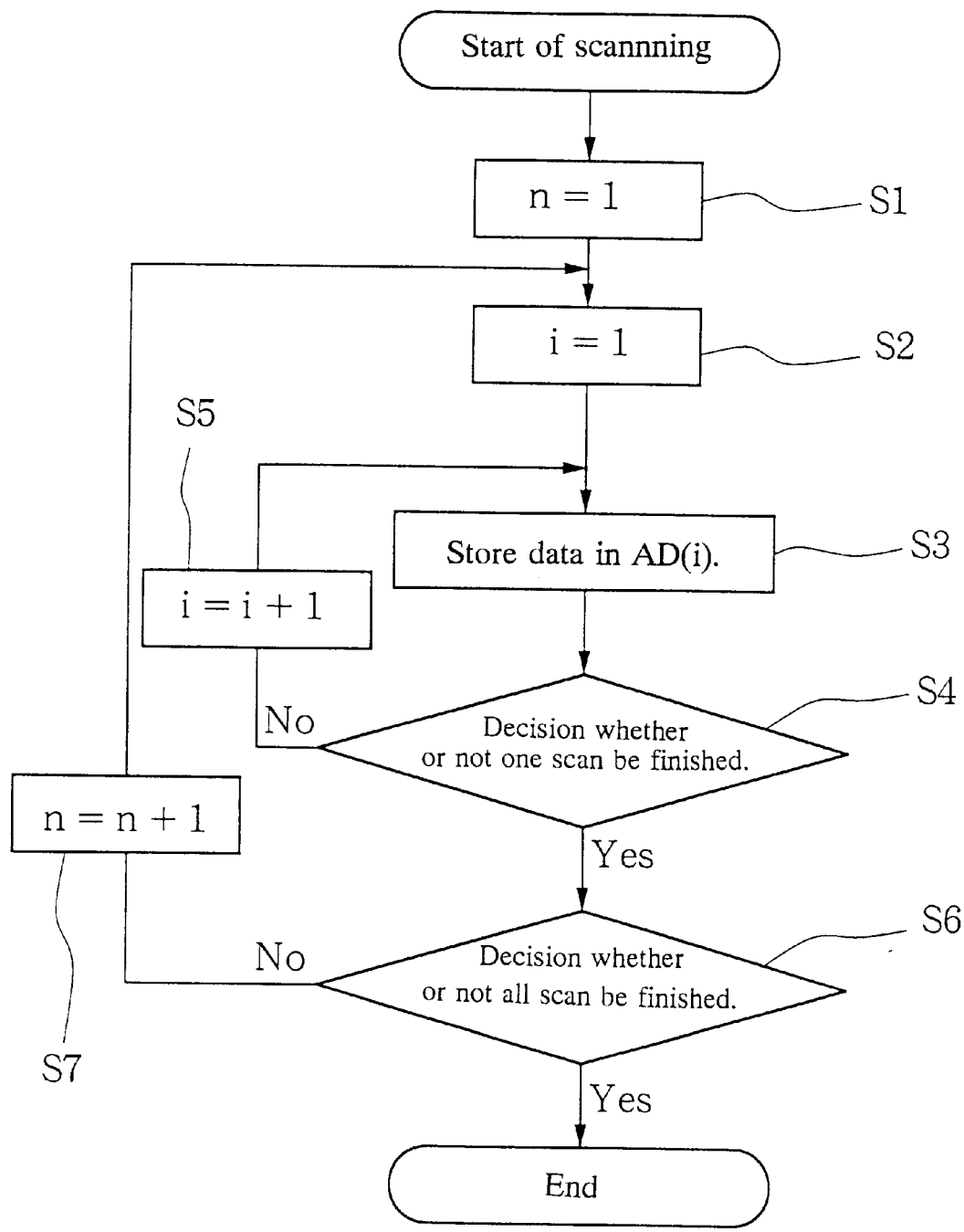
FIG. 15 is a flow chart of data storage in the embodiment 1B.
Figure 16:
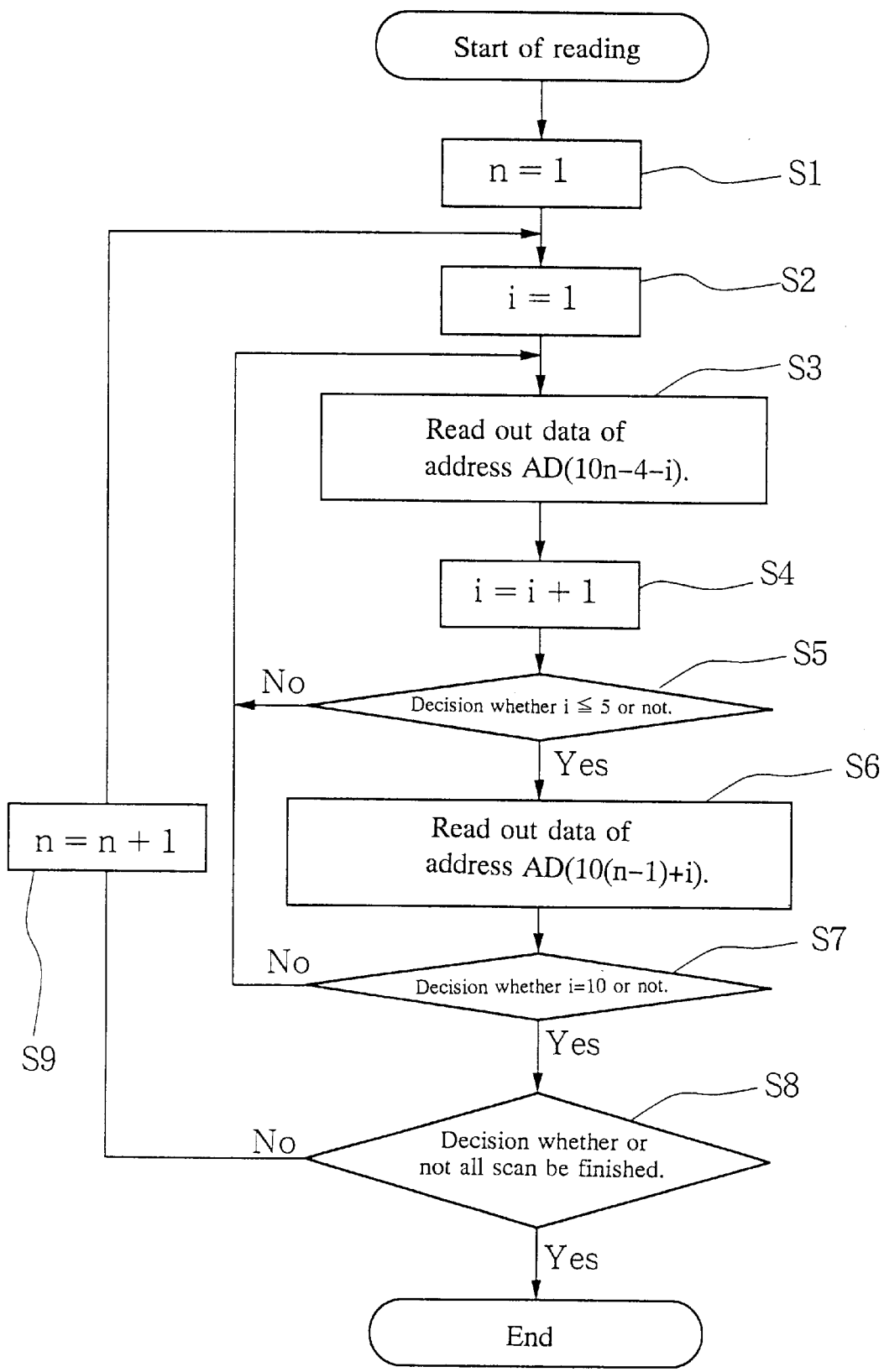
FIG. 16 is a flow chart of data reading in the embodiment 1B.

As processing therefor, "system that assignment of the memory address is made the prescribed order during the data reading" is shown in FIG. 15 and FIG. 16.

FIG. 15 is a flow chart for scan and storage, and FIG. 16 is a flow chart for reading. In FIG. 15, the data are stored in a memory in the order of scan.

S1: Scan times n be n=1.

S2: Number i be i=1.

S3: Store data of signals from a light receiving unit in AD(i) in sequence.

S4: Decision whether one scan be finished or not. If not finished, advance to S5, and if finished, advance to S6.

S5: i=i+1, and i is increased by 1. Decision whether or not i be 5 or less. As long as i is 5 or less, return to S3 and read out the data of the forward scan in the address decreasing direction. If i be more than 5, advance to S6.

S6: Decision whether all scan be finished or not. If not finished, advance to S7, and if finished, the process comes to the end.

S7: n=n+1, and n is increased by 1, and return to S2.

In FIG. 16, the data are read out from the memory in the prescribed order. Consequently signals of scattered lights (whole scan data) can be obtained in the state as if one scan line scans the wafer.

When the data are stored in the memory, signals from the photoelectric converter are stored in the state kept intact in a time series. In this case, the data are excluded from the storage object at the first half of the forward scan and at the first half of the rearward scan where the scanning is not made effective. Then the storage capacity of the memory can be utilized efficiently.

However, these data may be stored.

S1: Scan times n be n=1.

S2: Scan position i be i=1.

S3: Read out data in the forward scan. Read out data in AD (10n−4−i).

S4: Scan position be i=i+1, and i is increased by 1.

S5: Decision whether or not i be 5 or less. If i be 5 or less, return to S3, and read out the data in the forward scan in the address decreasing direction. If i be more than 5, advance to S6.

S6: Read out the data in the rearward scan in AD (10(n−1)+i) in the address increasing direction.

S7: Decision whether i=10 or not. That is, decision whether one scan be finished or not. If not finished, return to S3.

S8: Decision whether all scan be finished or not.

S9: If all scan be not finished, n=n+1 and n is increased by 1, and return to S2.

A specific example will be shown.

The data are stored in sequence in a time series.

On the other hand, when the data are read out, the address with the data in the forward scan (first half) stored therein is read out in the order of the address AD (10n−5−i) being the reverse order to the storage order.

The memory address corresponding to the data in the rearward scan is read out in the order of AD (10(n−1)+i) in the address increasing direction.

That is, the data from AD1 to AD5 being the memory address corresponding to the data in the forward scan are read out in sequence from AD5 in the address decreasing direction to AD1.

The data from AD6 to AD10 being the memory address corresponding to the data in the rearward scan are read out in sequence from AD6 in the address increasing direction to AD10.

A similar processing is to be repeated, from now on.

Thereby the data stored in the memory address can be treated as signals of scattered lights (whole scan data) obtained as if one scan line scanned the wafer.

In the embodiment 1B as above described, in order to minimize the region doubly acquiring the data, the inspection is started from the time when the luminous flux attains to the center line of the wafer.

Next, another embodiment 2B will be described.

The embodiment 2B is a modification of the signal processing unit.

That is, in order to treat the data as a time series data indicating from one end to the other end of the wafer, in a rearrangement of the data, "system that assignment of the memory address is made the prescribed order during the data storage" may be adopted separate from the embodiment 1B.

"System that assignment of the memory address is made the prescribed order during the data storage"

In this system, when the data are stored in the memory, the order of assignment of the memory is devised whereby the whole scan data can be formed.

Figure 17:
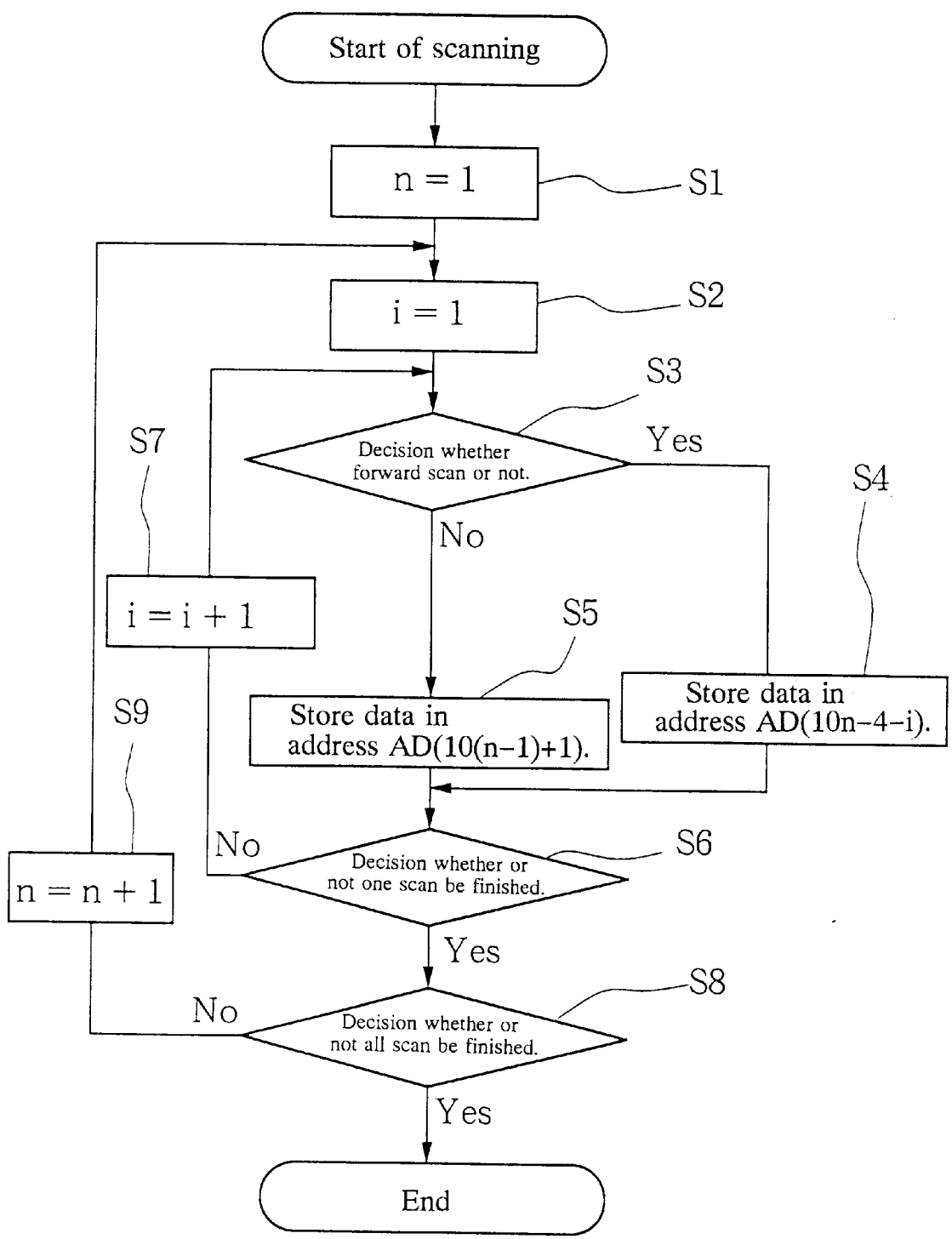
FIG. 17 is a flow chart of data storage in still another embodiment 2B of the invention.

This will be described in a flow chart of FIG. 17.

S1: Scan times n be n=1.
S2 Scan position i be i=1.
S3; Decision whether the forward scan or not.
S4: In the case of the forward scan, store the data in address AD (10n−4−i).
S5: In the case of the rearward scan, store the data in address AD (10(n−1)+i).
S6: Decision whether one scan be finished or not.
S7: If not finished, i=i+1 and i is increased by 1.
S8: Decision whether all scan be finished or not.
S9: If not finished, n=n+1 and n is increased by 1.

Figure 18:
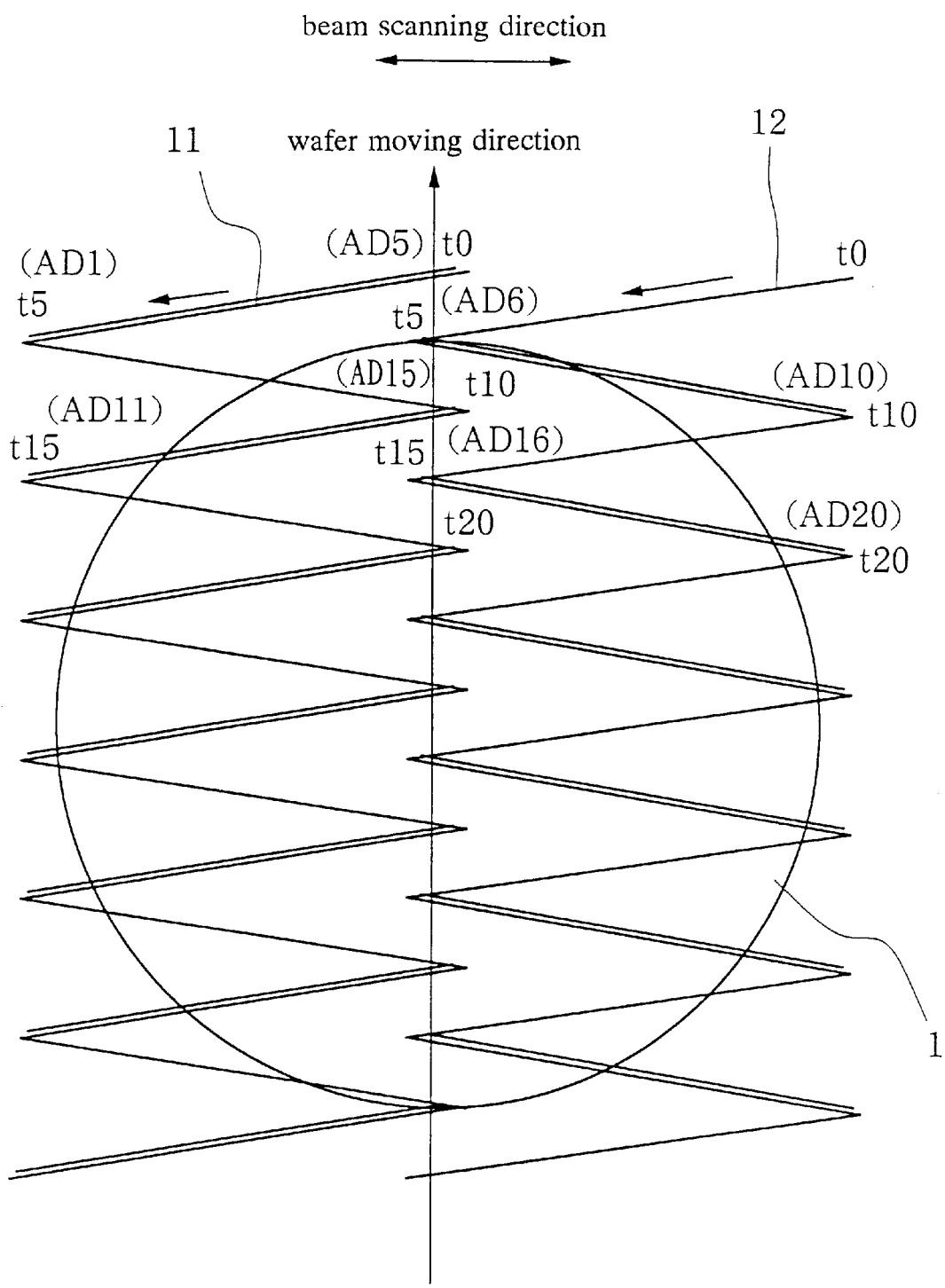
FIG. 18 is a diagram of data stored as data by a signal processing unit in the embodiment 2B shown on an object.

FIG. 18 shows a relation of the stored data and the address on the object.

Showing a specific example, the scan is started and for the period at the first half of the forward scan (t0≦t<t5), the data are stored in the order of address AD (10n−5−i) in the address decreasing direction.

Also for the period of the rearward scan (e.g., t5≦t<t10), the data are stored from the memory address AD6 to AD10 in sequence.

That is, in the period of the forward scan (t0≦t<t5), the output data of the light receiving unit are stored from the memory address AD5 to AD0 in sequence. In this case, the data are stored in the memory address decreasing direction.

For the period of the rearward scan (t5≦t<t10), the output data of the light receiving unit are stored from the memory address AD5 to AD0 in sequence. In this case, the data are stored in the memory address decreasing direction. a similar processing is to be repeated, from now on.

Thereby the data stored from the memory address AD1 to AD10 can be treated as signals of scattered lights (whole scan data) obtained as if one scan line scanned the wafer.

In this case, if the memory address is read out in sequence, the whole scan data can be obtained.

Next, another embodiment 3B will be described referring to FIG. 20.

The embodiment 3B is constituted such that one light source 21 is used and emitted lights are changed by a movable reflecting mirror 9. The movable reflecting mirror 9 is driven by a drive circuit 8.

As for the changing signal given to the drive circuit 8, signals similar to the signals shown in FIG. 13 may be used.

In the forward scan, the movable reflecting mirror gets into the optical path and reflects lights from the light source upward and makes the lights the first luminous flux. In the rearward scan, the movable reflecting mirror retreats from the optical path and the luminous flux advances in the state kept intact and becomes the second luminous flux.

Further, a modification will be described.

In the embodiment 1B, although the data at the latter half of the forward scan are connected with the data at the latter half of the rearward scan and the whole scan data are formed, regions overlapping each other may be provided so as to receive the data.

In this case, the data are compared in the overlapping regions whereby the connection of the data can be secured.

Figure 20:
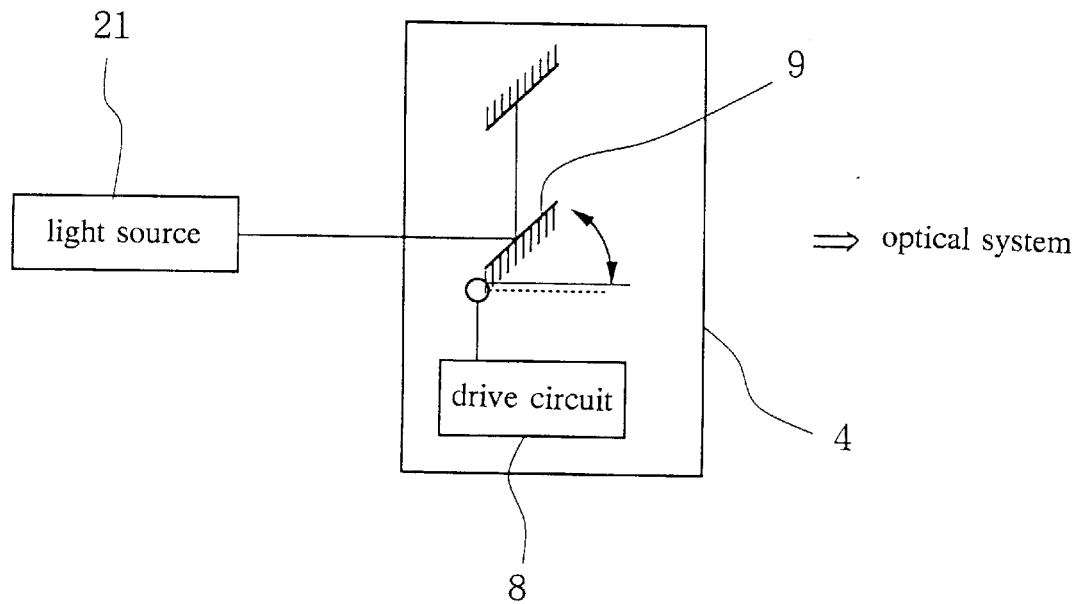
FIG. 20 is a diagram showing another example of a luminous flux changing means in the embodiment 2B.
Figure 21:
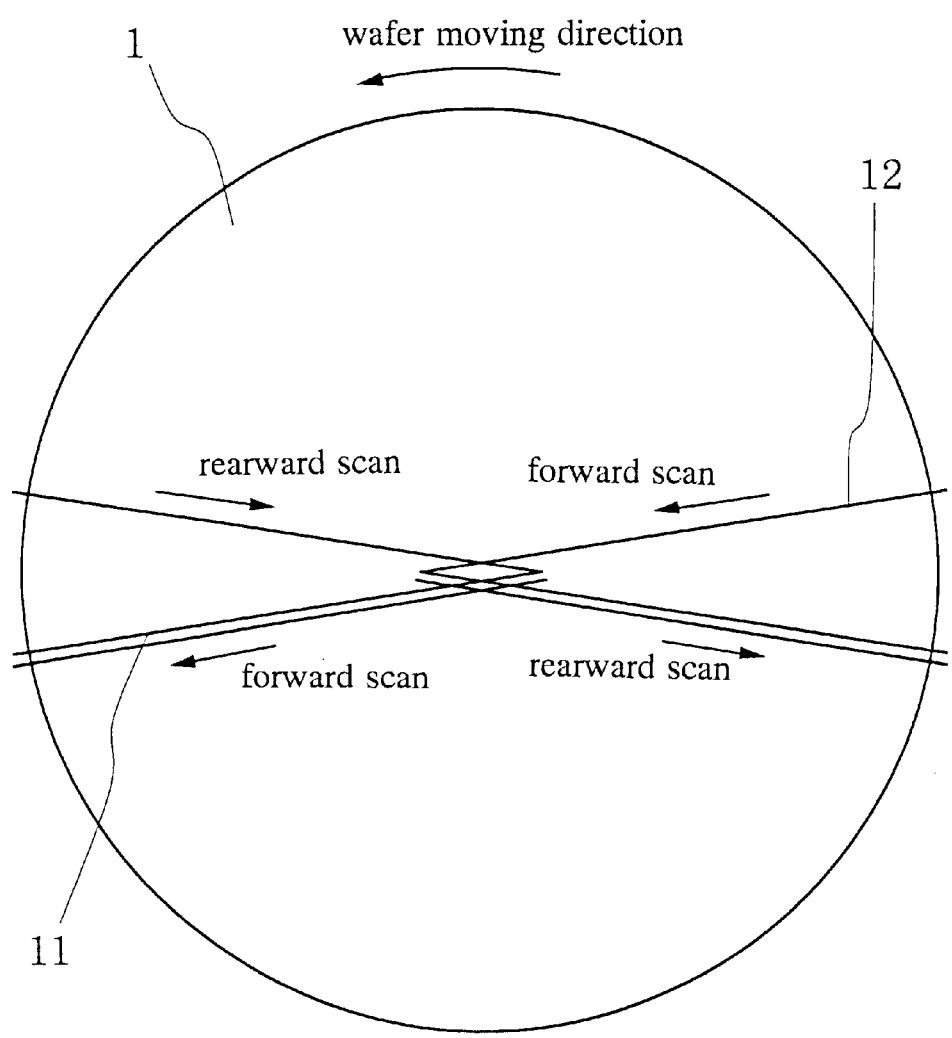
FIG. 21 is a diagram showing a modification of a system of rotating and moving a moving unit in the embodiment 2B.

Further as shown in FIG. 20, the moving unit can be constituted such that the stage is rotatably moved. Then in the case of the diameter address (180°), the data are rearranged suitably in a similar manner to the above-mentioned system. Also in the case of the radius address (360°), the address is caused to become large from the center towards the outside.

According to the surface inspection apparatus of the present invention, even a part near the edge of the wafer, which was not conventionally able to be inspected, so that the possibility of overlooking the generation of a foreign substance can be decreased.

Group C (FIGS. 22–31)

Figure 22:
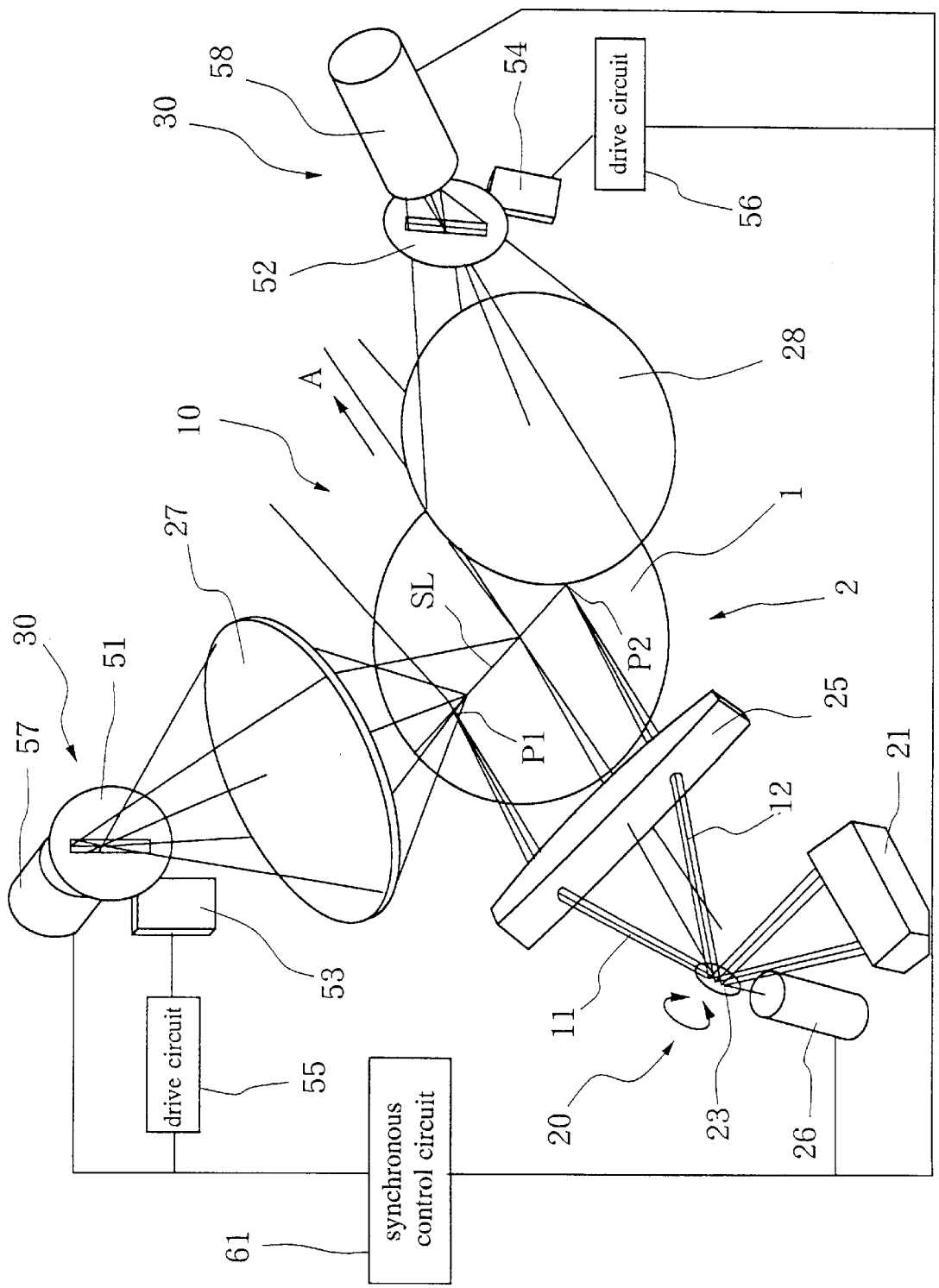
FIG. 22 is an optical arrangement diagram of still another embodiment 1C of the invention.
Figure 23:
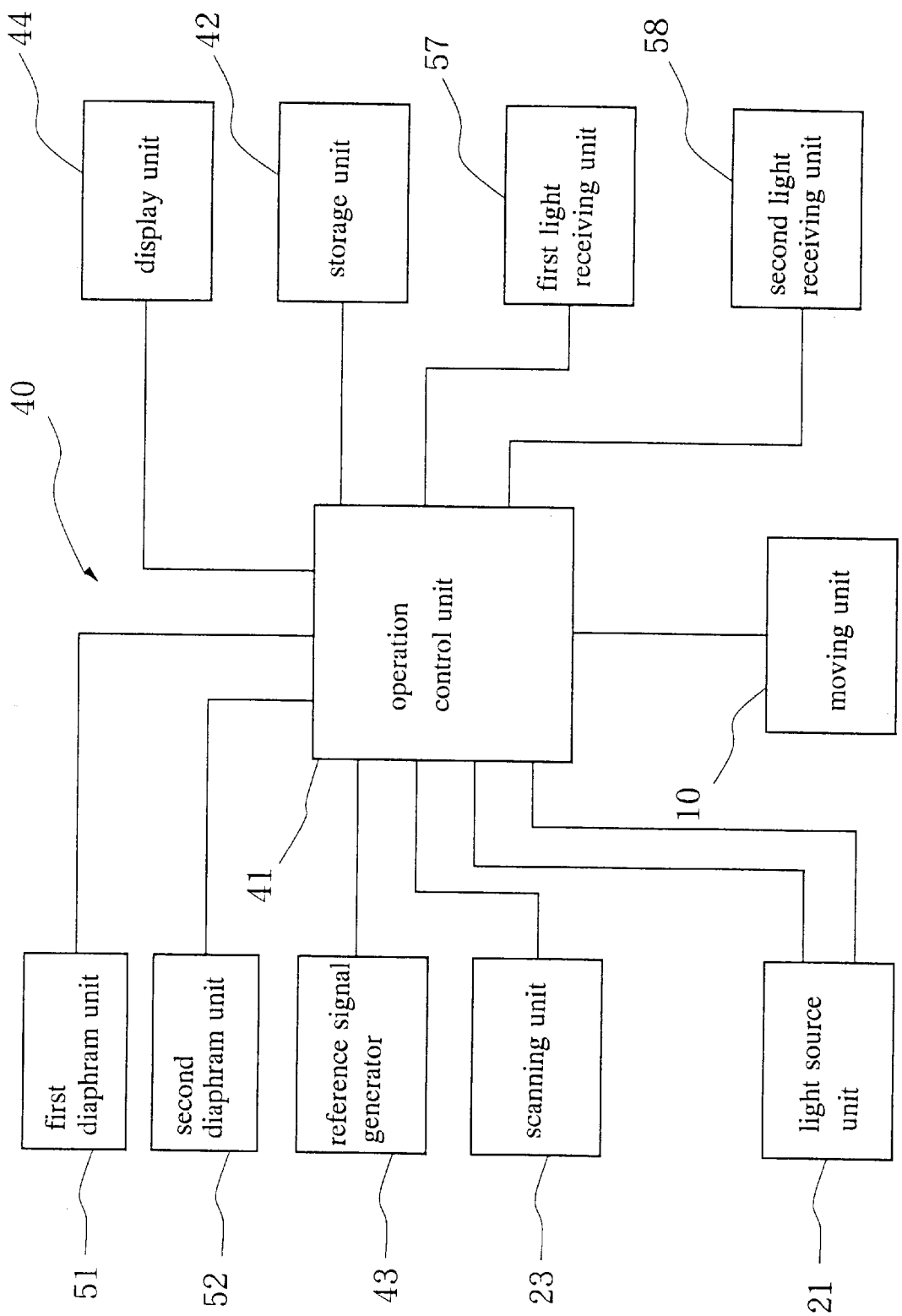
FIG. 23 is a block diagram of the embodiment 1C.

FIG. 22 is an optical arrangement diagram conceptually showing a surface inspection apparatus according to still another embodiment 1C of the present invention, and FIG. 23 is a block diagram of the surface inspection apparatus.

The surface inspection apparatus of the embodiment 1C comprises a moving unit 10, an optical system 20, a light receiving unit 30 and a signal processing unit 40.

The moving unit 10 is constituted by a stage 2 movable forward and rearward at least in one direction. The stage 2 moves an object of inspection such as a wafer 1 in definite slow speed in the direction of arrow A shown in FIG. 22.

The optical system 20 is provided with a light source unit 21, a scanning mirror 23, a convergent lens 25 and a condenser lens 27.

The light source unit 21 is provided with first and second laser beam beam sources being strong in intensity, such as a semiconductor laser, and is arranged such that luminous flux 11 and luminous flux 12 of the first and second laser beam sources divide into substantially two regions the surface of the wafer 1 being an inspection object and are caused to be incident in the direction capable of scanning respectively.

Figure 24:
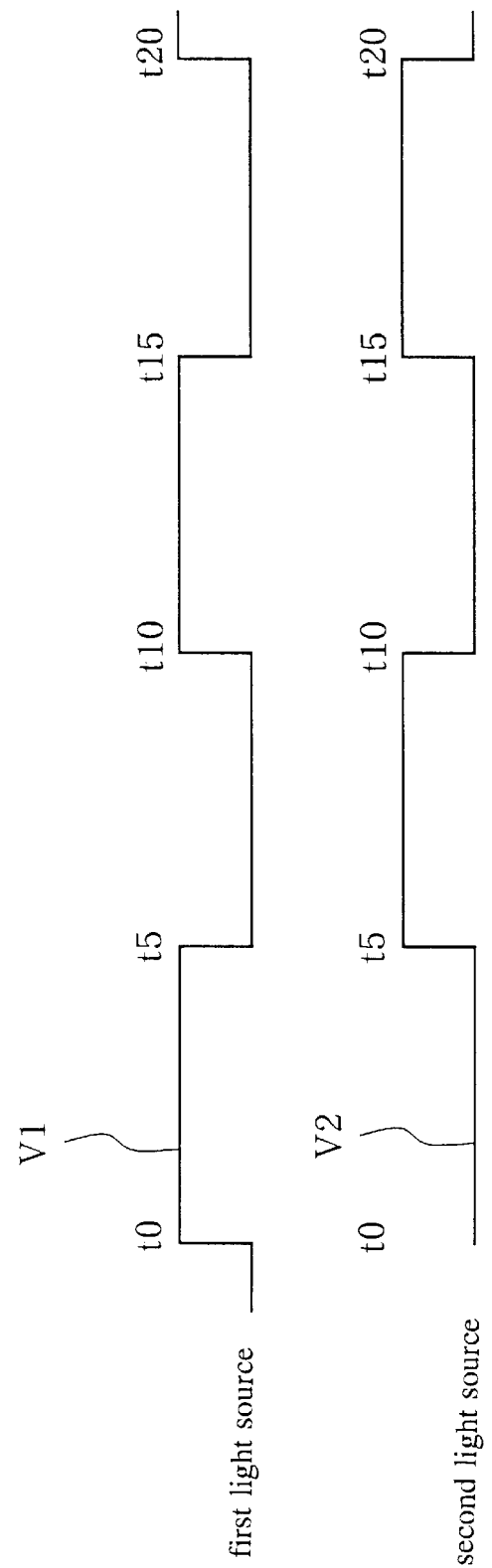
FIG. 24 is a wave form chart of a light source drive signal in the embodiment 1C.

Based on signals V1, V2 shown in FIG. 24, the first light source and the second light source are lit alternately, and at the forward scan (t0–t5), the luminous flux 11 emitted from the light source unit 21 scans, while at the rearward scan (t5–t10), the luminous flux 12 emitted from the light source unit 21 scans.

The scanning mirror 23 is rotated by a motor 26 corresponding to a scanning unit in response to signals from a synchronous control circuit 61 of an operation control unit 41, and moves the luminous flux emitted from the light source unit 21 forward and rearward.

The convergent lens 25 converges the first luminous flux 11 and the second luminous flux 12 emitted from the light source unit 21 onto the wafer 1 being the object, and forms spots P1 and P2. The spots P1 and P2 are scanned linearly by the rotation of the scanning mirror 23 and a scan line SL is formed.

The condenser lenses 27 and 28 collect lights scattered by a foreign substance on the wafer onto a light receiving surface of a photoelectric converter. The condenser lenses 27 and 28 are arranged in the direction and position where regular reflection lights by the scan lights generated from the light source unit 21 and reflected in regular reflection on the wafer surface is not incident.

Next a scanning method by the optical system will be described.

In the embodiment of this group, the scan from the right to the left is made forward scan and the scan from the left to the right is made rearward scan. Also in FIG. 25, the left side is made the first luminous flux side and the right side is made the second luminous flux side.

Figure 25:
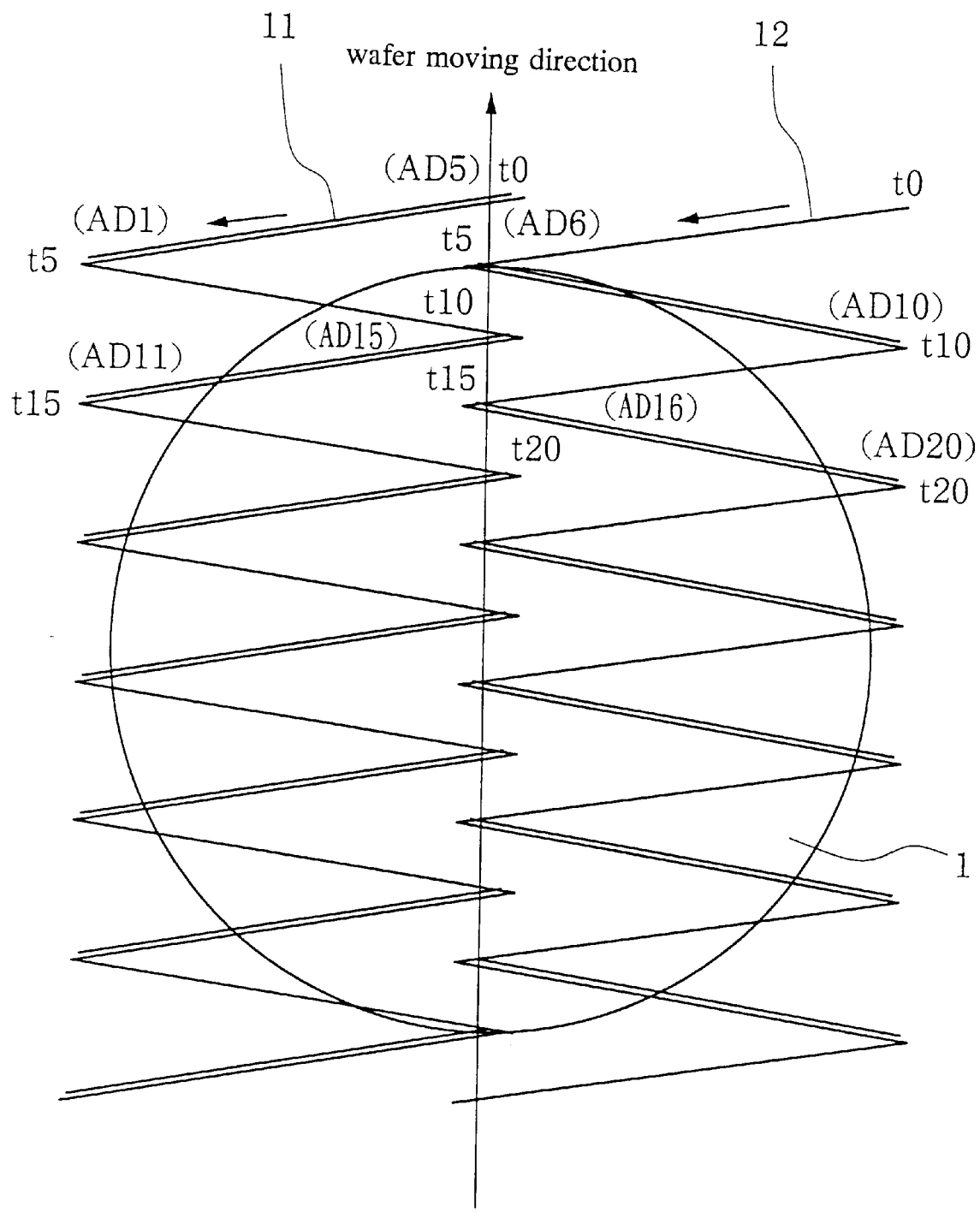
FIG. 25 is a diagram of data stored as data by a signal processing unit in the embodiment 1C shown on an object.

Consequently in the forward scan, the first light source is lit and the first luminous flux 11 scans, and in the rearward scan, the second light source is lit and the second luminous flux 12 scans. In FIG. 25, in order to make the explanation clear, the scan line is written coarsely. In the actual state, however, the beams scan the whole surface of the wafer 1 densely.

Explaining the first luminous flux side taken as an example, the beams strike the edge and the strong scattered lights are produced in the vicinity of the end of the forward scan or on the midway of the forward scan, however, since the rear side from this position corresponds to the outside of the wafer and need not be inspected, the inspection is not hindered. That is, while the strong scattered lights are produced in the vicinity of the end of the forward scan of the beam or on the midway of the forward scan and the photoelectric converter 31 described later does not act normally, no problem is offered since the spot P1 is moved on the outside of the wafer and at a part of the rearward path (transition area). Also even if there is a substance immediately outside the wafer to be inspected so that the luminous flux strikes the substance and the scattered lights are produced, the inspection is not hindered on account of a similar reason, and this serves to decrease restrictions on making the apparatus.

Diaphragm units 51 and 52 are provided on this side of the light receiving unit in order that only scattered lights from the prescribed scan region within the detection object range is securely received in the light receiving unit. The diaphragm units 51, 52 can be constituted, for example, by a flat plate having a slit.

The diaphragm units 51 and 52 are provided with drive units 53 and 54 controlled by drive circuits 55 and 56. A synchronous control circuit 61 is connected to the drive circuits 55 and 56.

Figure 26:
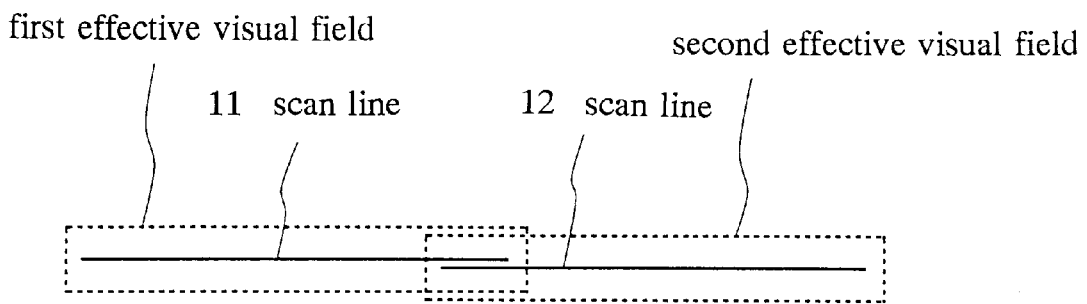
FIG. 26 is a diagram showing a position relation of first and second field stops in the embodiment 1C.

As the scan lights are moved, a field stop 51 for the first scan luminous flux is moved to the left side and a field stop 52 for the second scan luminous flux is moved to the right side. The moving directions are coincident with the direction from the center of the object towards the outside. As shown in FIG. 26, the first detection object range and the second detection object range slightly overlap each other on the object.

Figure 27:
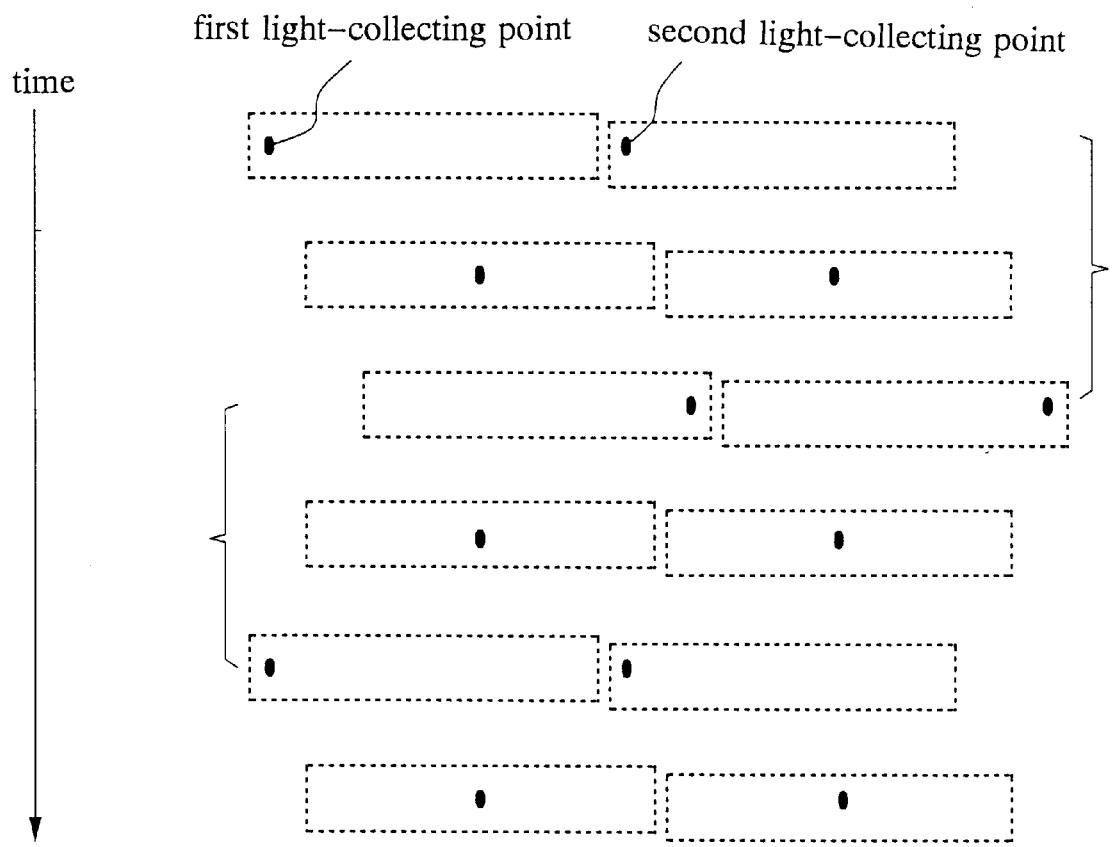
FIG. 27 is a diagram showing moved positions of the first and second field stops in the embodiment 1C.

Therefore the field stops are moved as shown in FIG. 27 so that scattered lights by other scan luminous flux are not received by other photoelectric converter in the overlapping ranges.

Figure 28:
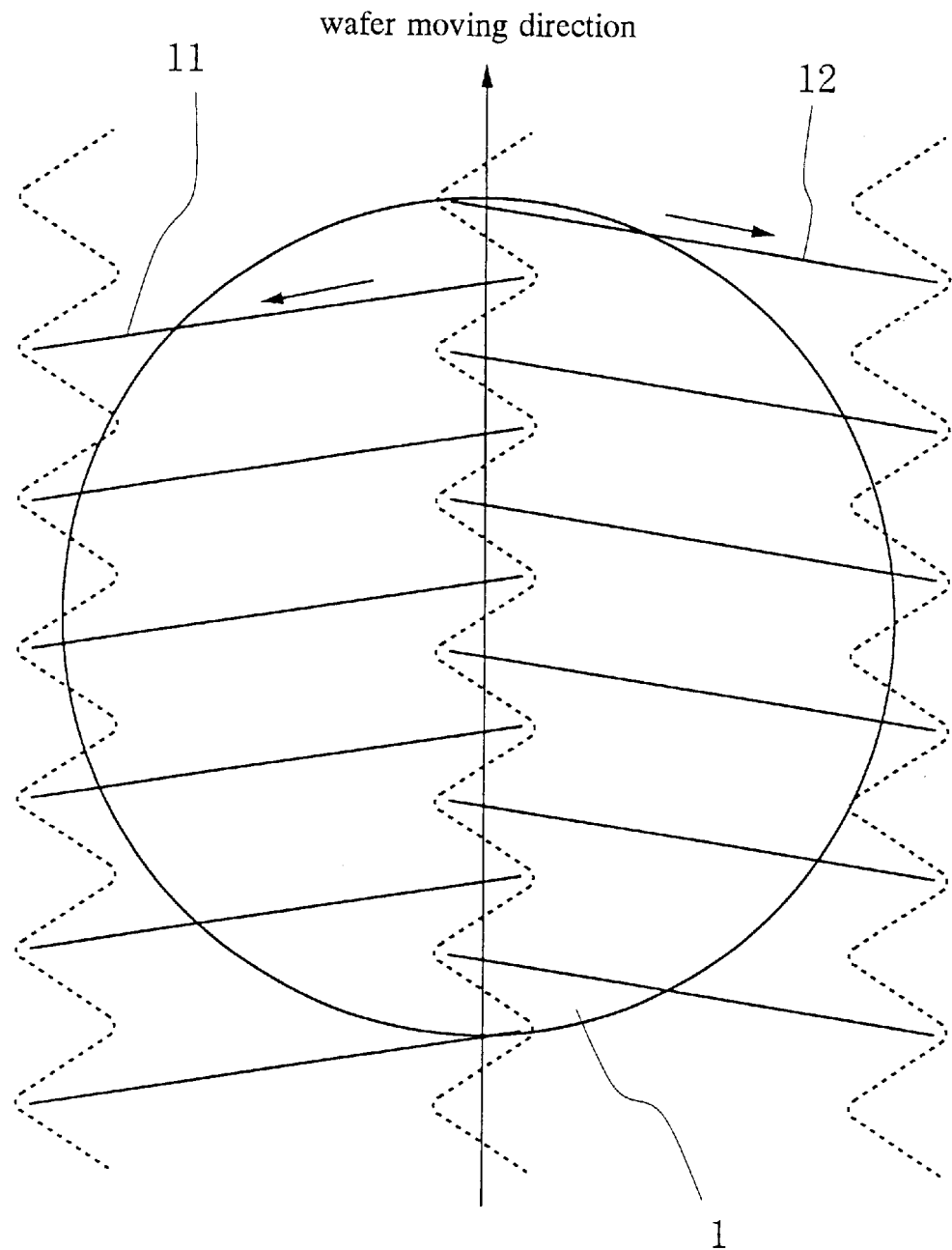
FIG. 28 is a diagram of moved positions of the first and second field stops in the embodiment 1C shown on a wafer.

FIG. 28 shows the moving of the field stops on the object, that is, the wafer.

The light receiving units 57 and 58 have the first and second photoelectric converters respectively. Scattered lights in the first area are received by the first photoelectric converter received through the first condenser lens 27. Also scattered lights in the second area are received by the second photoelectric converter received through the second condenser lens 28. A synchronous control circuit 61 is connected to the light receiving units 57 and 58.

As for the photoelectric converter, for example, a photomultiplier may be utilized. The diaphragm units 51 and 52 are controlled such that in the forward scan, scattered lights by the first luminous flux are received, and in the rearward scan, scattered lights by the second luminous flux are received.

The signal processing unit 40 is provided with an operation control unit 41, a storage unit 42, a reference signal generator 43 and a display unit 44.

As above described, according to the function of the diaphragm units 51 and 52, since only the data of the forward scan are fetched on the first luminous flux side and only the data of the rearward scan are fetched on the second luminous flux side, signals do not appear in the order of scanning by one scan line. Consequently in order to treat the data as time series data indicating from one end to other end of the wafer, the devising such as rearrangement of the data is required.

That is, for the period from t0 to t5, data of scattered lights do not appear, and for the period from t5 to t10, data of scattered lights from the position L5 to the position L10 appear in sequence.

For the period for t10 to t15, data of scattered lights do not appear, and for the period from t15 to t20, data of scattered lights from the position L15 to the position L20 appear in sequence.

Since an interval between the scan lines in the actual state is narrow, the data order at the latter half of the rearward scan is reversed, and the data for the period from t20 to t15 can be connected with the data for the period from t5 to t10. Then the data can be treated as if one scan line scanned the wafer and the signals of the scattered lights (whole scan data) could be obtained.

Figure 29:
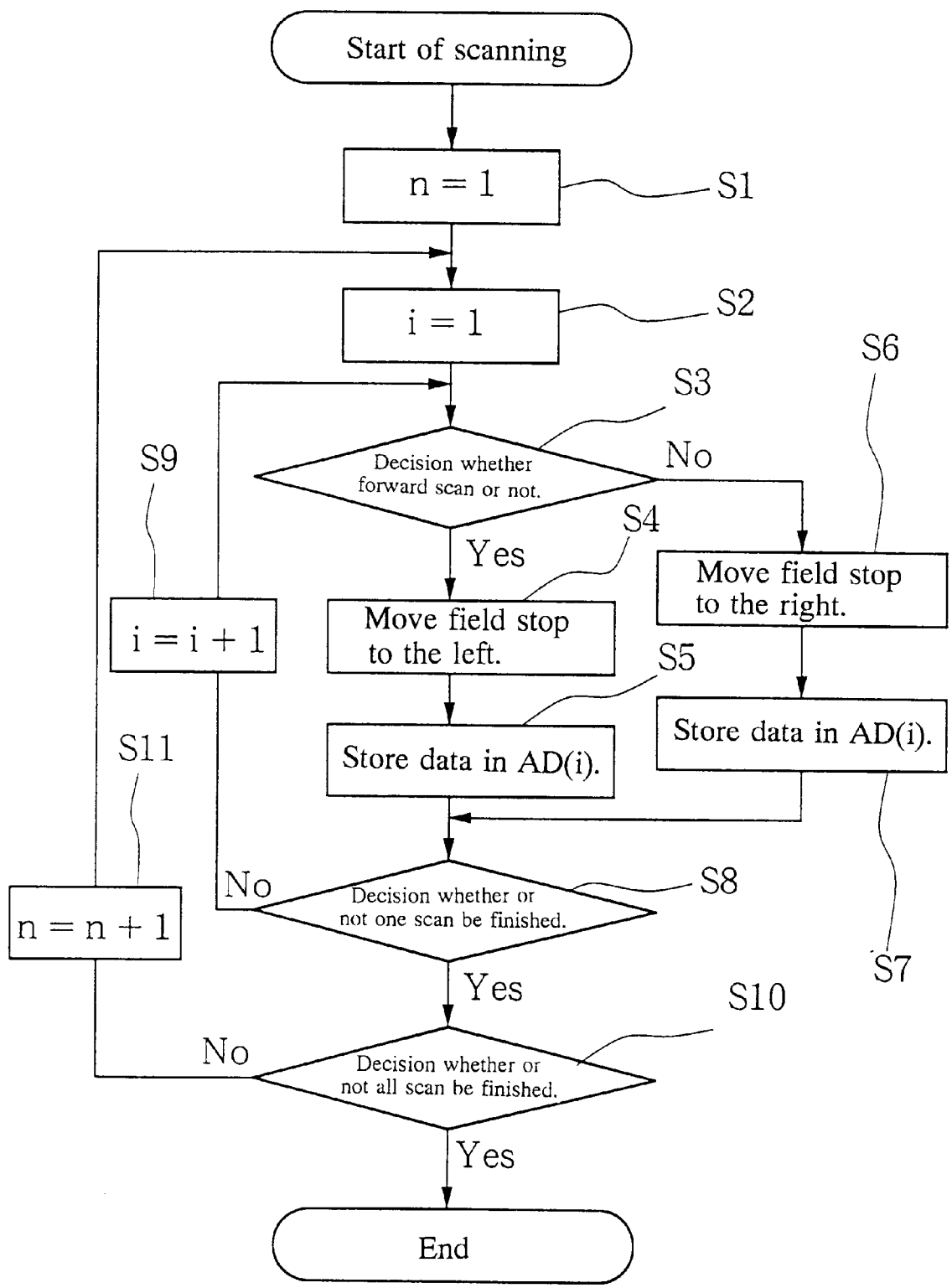
FIG. 29 is a flow chart of data storage in the embodiment 1C.
Figure 30:
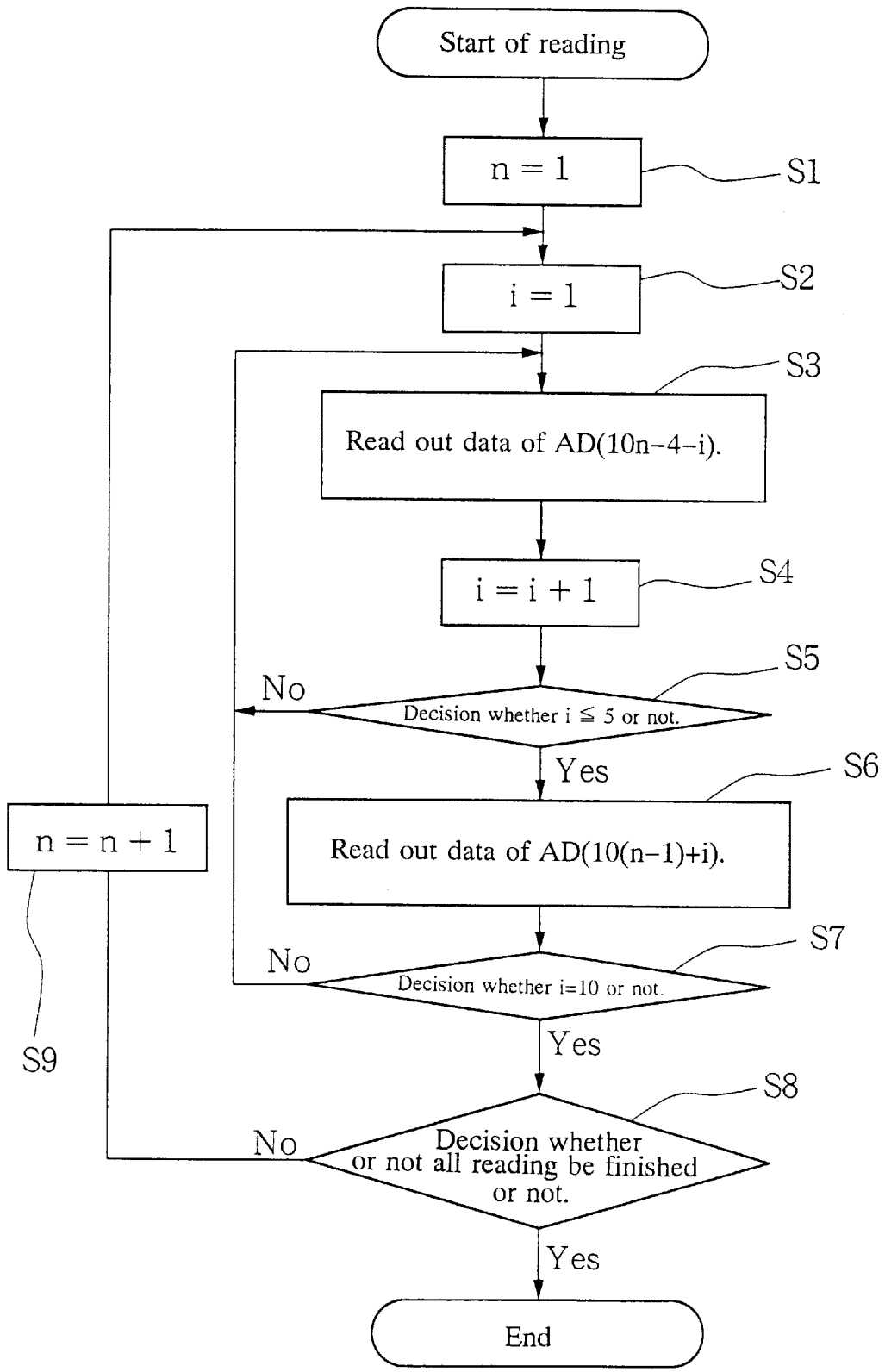
FIG. 30 is a flow chart of data reading in the embodiment 1C.

As processing therefor, "system that assignment of the memory address is made the prescribed order during the data reading" is shown in FIG. 29 and FIG. 30.

FIG. 29 is a flow chart for scan and storage, and FIG. 30 is a flow chart for reading.

In FIG. 29, the data are stored in a memory in the order of scan.

S1: Scan times n be n=1.

S2: Number i be i=1.

S3: Decision whether the forward scan or not. If the forward scan, advance to S4, and if the rearward scan, advance to S6.

S4: Move the field stop to the left.

S5: Store the signal data from the light receiving unit in AD(i) in sequence.

S6: In the case of the rearward scan, move the field stop to the rignt.

S7: Store the signal data from the light receiving unit in AD(i) in sequence.

S8: Decision whether one scan be finished or not. If not finished, advance to S9, and if finished, advance to S10.

S9: i=i+1, and i is increased by 1, and return to S3.

S10: Decision whether all scan be finished or not. If not finished, advance to S11, and if finished, the process is ended.

S11: n=n+1, and n is increased by 1, and return to S2.

In FIG. 30, the data are read out from the memory in the prescribed order, and the signals of the scattered lights (whole scan data) can be obtained as if one scan line scanned the wafer.

When the data are stored in the memory, signals from the photoelectric converter are stored in the state kept intact in a time series. In this case, the data are excluded from the storage object at the first half of the forward scan and at the first half of the rearward scan where the scanning is not made effective. Then the storage capacity of the memory can be utilized efficiently.

However, these data may be stored.

S1: Scan times n be n=1.

S2: Scan position i be i=1.

S3: Read out the data in the forward scan. Read out AD (10n−4−i).

S4: Scan position be i=i+1, and i is increased by 1.

S5: Decision whether or not i be 5 or less. If 5 or less, return to S3, and read out the data in the forward scan in the address decreasing direction. If i be more than 5, advance to S6.

S6: Read out the data in the rearward scan in AD (10(n−1)+i) in the address increasing order.

S7: Decision whether i=10 or not. That is, decision whether one scan be finished or not. If not finished, return to S3.

S8: Decision whether all scan be finished or not.

S9: If not finished, n=n+1, and n is increased by 1, and return to S2.

A specific example will be shown.

The data are stored in sequence in a time series.

On the other hand, when the data are read out, the address with the data in the forward scan (first half) stored therein is read out in the order of the address AD (10n−4−i) being the reverse order to the storage order.

The memory address corresponding to the data in the rearward scan is read out in the address increasing order AD (10(n−1)+i).

That is, the data from AD1 to AD5 being the memory address corresponding to the data in the forward scan are read out in sequence from AD5 in the address decreasing direction to AD1.

The data from AD6 to AD10 being the memory address corresponding to the data in the rearward scan are read out in sequence from AD6 in the address increasing direction to AD10.

A similar processing is to be repeated, from now on.

Thereby the data stored in the memory address can be treated as signals of scattered lights (whole scan data) obtained as if one scan line scanned the wafer.

Next, another embodiment 2C will be described.

The embodiment 2C is a modification of the signal processing unit.

That is, in order to treat the data as time series data indicating from one end to the other end of the wafer, in rearrangement of the data, "system that assignment of the memory address is made the prescribed order during the data reading" may be adopted separate from the embodiment 1C.

"System that assignment of the memory address is made the prescribed order during the data storage"

In this system, when the data are stored in the memory, the order of assignment of the memory address is devised whereby the whole scan data can be formed.

Figure 31:
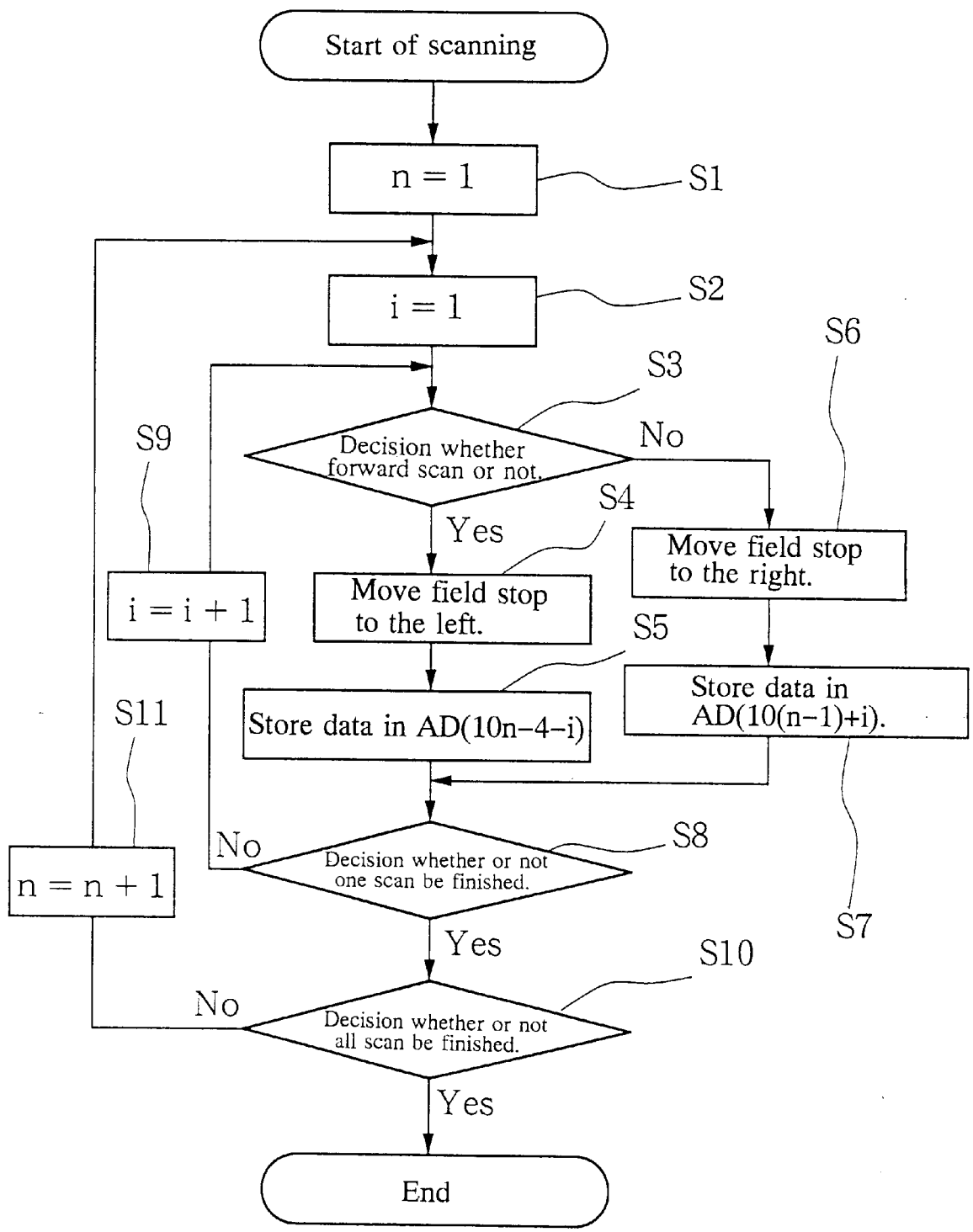
FIG. 31 is a flow chart of data storage in still another embodiment 2C of the invention.
Figure 32:
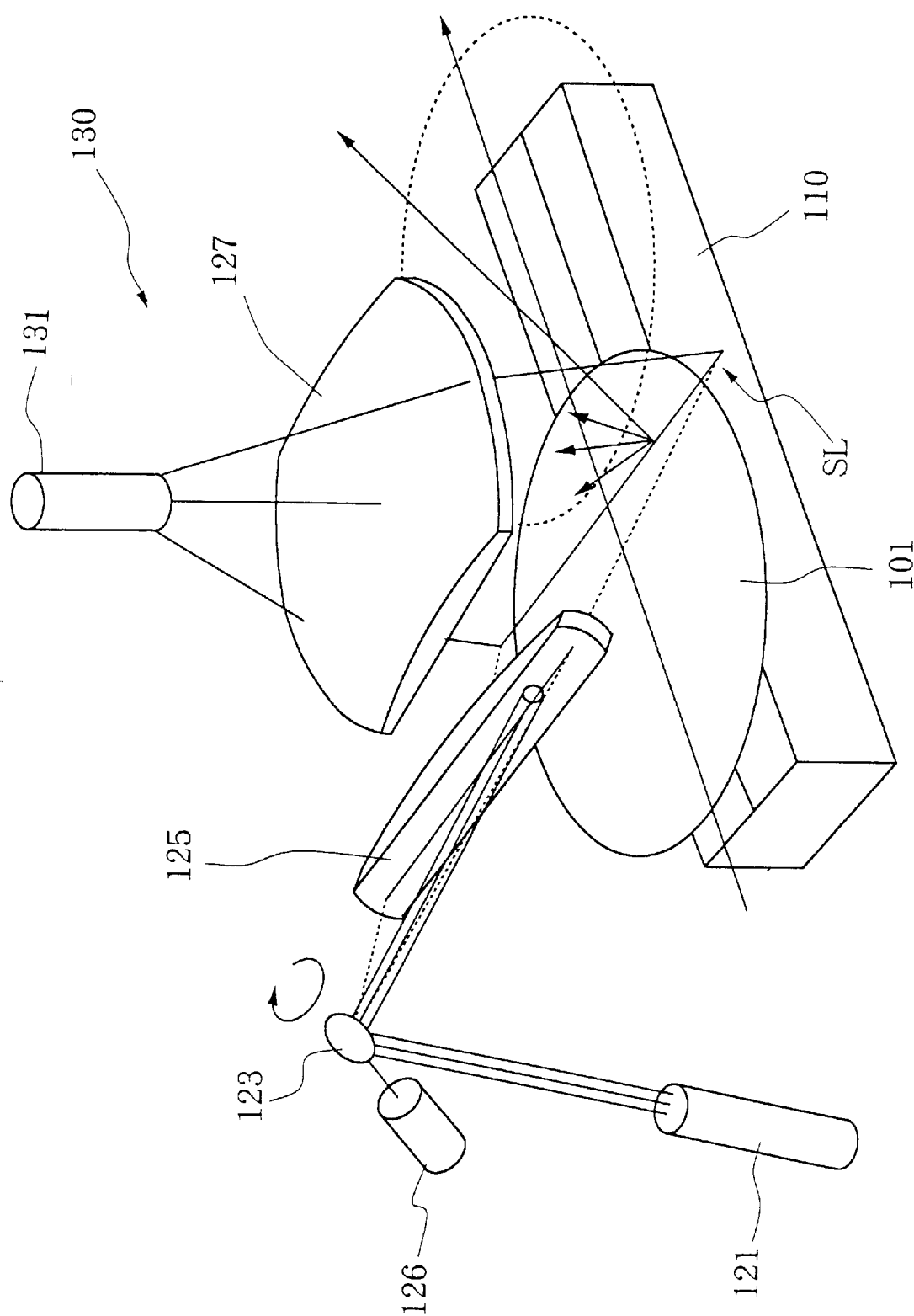
FIG. 32 is a schematic configuration diagram of a wafer surface inspection apparatus in the prior art.

This will be explained in a flow chart of FIG. 31.

S1: Scan times n be n=1.

S2: Scan position i be i=1.

S3: Decision whether the forward scan or not. If the forward scan, advance to S4, and if the rearward scan, advance to S6.

S4: Move the field stop to the left.

S5: Store the signal data from the light receiving unit in AD (10n−4−i) in sequence.

S6: In the case of the rearward scan, move the field stop to the right.

S7: Store the signal data from the light receiving unit in AD (10(n−1)+i) in sequence.

S8: Decision whether one scan be finished or not. If not finished, advance to S9, and if finished, advance to S10.

S9: i=i+1, and i is increased by 1, and return to S3.

S10: Decision whether all scan be finished or not. If not finished, advance to S11, and if finished, the process is ended.

S11: n=n+1, and n is increased by 1, and return to S2.

Showing a specific example, the scan is started and for the period at the first half of the forward scan (t0≦t<t5), the data are stored in the order of address AD (10n−5−i) in the address decreasing direction.

Also the data for the period of the rearward scan (e.g., t5≦t<t10) are stored from the memory address AD6 to AD10 in sequence.

That is, for the period of the forward scan (t0≦t<t5), the output data of the light receiving unit are stored from the memory address AD5 to AD1 in sequence. In this case, the data are stored in the memory address decreasing direction.

For the period of the rearward scan (t5≦t<t10), the output data of the light receiving unit are stored from the memory address AD5 to AD1 in sequence. In this case, the data are stored in the memory address decreasing direction.

A similar processing is to be repeated, from now on.

Thereby the data stored from the memory address AD1 to AD10 can be treated as signals of scattered lights (whole scan data) obtained as if one scan line scans the wafer.

In this case, if the memory address is read out in sequence, the whole scan data can be obtained.

A modification will be described.

In the embodiment 1C, although the data at the latter half of the forward scan are connected with the data at the latter half of the rearward scan so that the whole scan data are formed, regions overlapping each other may be provided so as to receive the data. In this case, the data in the overlapping regions are compared whereby the connection of the data can be secured.

Further in the invention of the group C, constitution as shown in FIGS. 18–21 can be performed.

What is claimed is:

1. A surface inspection apparatus comprising:

a light source;

a scan optical system for scanning a surface of an object in a direction of crossing the object by luminous flux from said light source;

a moving unit for moving the object relatively in a direction of a prescribed angle with respect to the scanning direction;

a light receiving unit having a photoelectric converter for receiving scattered lights from the surface of the object; and a signal processing unit for performing the surface inspection based on signals from said light receiving unit, wherein said optical system is controlled to scan the luminous flux in forward and rearward directions, and said signal processing unit performs the surface inspection, based on both signals of said light receiving unit in a region excluding a transition area where scan is performed from the outside of the object to the object, within the forward scan region by the scan optical system, and signals of said light receiving unit in a region excluding a transition area where scan is performed from the outside of the object to the object, within the rearward scan region by the scan optical system.

2. A surface inspection apparatus as set forth in claim 1, wherein said signal processing unit performs the surface inspection based on signals of the light receiving unit at the latter half of the forward scan and at the latter half of the rearward scan by the scan optical system.

3. A surface inspection apparatus as set forth in claim 2, wherein said signal processing unit includes a signal storage unit for storing signals of the light receiving unit, and said signal storage unit stores data at the latter half of the forward scan of the scan optical system in the scan order and stores data at the latter half of the rearward scan of the scan optical system in the reverse order to the scan order, whereby signals of the light receiving unit are read out in a similar order to that in the case of scanning in such a manner as to cross the object.

4. A surface inspection apparatus as set forth in claim 2, wherein said signal processing unit includes a signal storage unit for storing signals of the light receiving unit, and said signal storage unit stores data from the light receiving unit in the receiving order, and when the data are read out, said signal storage unit outputs the data at the latter half of the forward scan of the scan optical system in the scan order and outputs the data at the latter half of the rearward scan in the reverse order to the scan order, whereby the data of the light receiving unit are outputted in a similar order to that in the case of scanning in such a manner as to cross the object.

5. A surface inspection apparatus as set forth in claim 1, wherein said light source unit is controlled to be lit in a region excluding a transition area where scan is performed from the outside of the object to the object, within the forward and rearward scan region by the scan optical system and to be put out in a region including the transition area other than the lighting region, and said signal processing unit performs the surface inspection, based on signals of the light receiving unit in a region excluding a transition area where scan is performed from the outside of the object to the object, within the forward and rearward scan region by the scan optical system.

6. A surface inspection apparatus comprising:

a light source;

a scan optical system for scanning a surface of an object in a direction of crossing the object by luminous flux from said light source;

a moving unit for moving the object relatively in a direction of a prescribed angle with respect to the scanning direction;

a light receiving unit having a photoelectric converter for receiving scattered lights from the surface of the object; and a signal processing unit for performing the surface inspection based on signals from said light receiving unit, wherein said scanning means is controlled to scan the luminous flux in forward and rearward directions, and said signal processing unit changes the arrangement of signals from said light receiving unit, and performs the surface inspection, based on signals of said light receiving unit in a region excluding a transition area where scan is performed from the outside of the object to the object, within the forward and rearward scan region by the scan optical system or the signals of said light receiving unit in a region excluding a transition area where scan is performed from the outside of the object to the object, within the rearward scan region by the scan optical system, and performs the surface inspection based on the arranged signals.

7. A surface inspection apparatus comprising:

a light source;

a scan optical system for scanning luminous flux from said light source and converging the luminous flux onto a surface to be inspected;

a moving unit for moving the surface of the inspection object in a direction different from the scan direction of said scan optical system;

a light receiving unit having a photoelectric converter for receiving scattered lights from the converging point of the luminous flux; and a signal processing unit for processing signals from said light receiving unit, wherein said scan optical system performs scan forward and rearward by two luminous flux, and said signals processing unit performs the signal processing based on a signal with one of the forward scan or rearward scan in a direction of the one luminous flux travelling from the object towards the outside of the object and on a signal with one of the forward scan or rearward scan in a direction of the other luminous flux travelling from the object towards the outside of the object.

8. A surface inspection apparatus as set forth in claim 7, wherein said scan optical system is provided with a synchronizing means for control, so that at one of the two converging points moving forward and rearward, the scanning is made effective in the forward scan, and at the other of the two converging points moving forward and rearward, the scanning is made effective in the rearward scan.

9. A surface inspection apparatus as set forth in claim 8, wherein said light source unit includes one light source, and said synchronizing means can change luminous flux from the light source toward the two scan optical systems.

10. A surface inspection apparatus as set forth in claim 8, wherein said light source unit includes at least two light sources of the same wavelength, and said synchronizing means is provided with shutters in the optical path of the scan luminous flux from the two light sources.

11. A surface inspection apparatus comprising;

a light source;

a scan optical system having a scanning means for scanning luminous flux from said light source in one direction, and scanning a surface to be inspected;

a moving unit for moving the surface to be inspected in a direction orthogonal to the scan direction of said scan optical system;

a light receiving unit having a photoelectric converter for receiving scattered lights from the converging point; and a signal detector for detecting signals from said light receiving unit, wherein said scan optical system scans linearly in parallel two luminous flux of the same wavelength, and said light receiving unit and said signal detecting unit are constituted by two light receiving units for separately receiving scattered lights from the converging points produced by the two luminous flux, and a diaphragm unit is arranged to each light receiving unit so that only scattered lights in a prescribed region are received and a position of the diaphragm unit is varied in response to the scan of the luminous flux.

12. A surface inspection apparatus as set forth in claim 11, wherein the position of said diaphragm unit is varied in synchronization with the scan luminous flux.

13. A surface inspection apparatus as set forth in claim 11, wherein the prescribed region of each light receiving unit for receiving light is a part of the object, and the whole object is covered with the prescribed region of each light receiving unit.

* * * * *